(12) United States Patent
Kim et al.

(10) Patent No.: US 10,956,764 B2
(45) Date of Patent: Mar. 23, 2021

(54) ELECTRONIC DEVICE COMPRISING BIOMETRIC SENSOR

(71) Applicant: Samsung Electronics Co., Ltd., Gyeonggi-do (KR)

(72) Inventors: Joo Han Kim, Gyeongsangbuk-do (KR); Jin Man Kim, Gyeongsangbuk-do (KR); Byung Kyu Kim, Gyeongsangbuk-do (KR); Jin Woo Park, Gyeongsangbuk-do (KR); Young Bae Sim, Gyeongsangbuk-do (KR); Yeun Wook Lim, Daegu (KR)

(73) Assignee: Samsung Electronics Co., Ltd., Gyeonggi-Do (KR)

( * ) Notice: Subject to any disclaimer, the term of this patent is extended or adjusted under 35 U.S.C. 154(b) by 0 days.

(21) Appl. No.: 16/499,938

(22) PCT Filed: Apr. 10, 2018

(86) PCT No.: PCT/KR2018/004205
§ 371 (c)(1),
(2) Date: Oct. 1, 2019

(87) PCT Pub. No.: WO2018/190619
PCT Pub. Date: Oct. 18, 2018

(65) Prior Publication Data
US 2020/0057902 A1    Feb. 20, 2020

(30) Foreign Application Priority Data
Apr. 11, 2017 (KR) .................. 10-2017-0046973

(51) Int. Cl.
*G06K 9/20* (2006.01)
*G06K 9/00* (2006.01)
*H04N 5/225* (2006.01)

(52) U.S. Cl.
CPC ......... *G06K 9/209* (2013.01); *G06K 9/00013* (2013.01); *H04N 5/2257* (2013.01)

(58) Field of Classification Search
None
See application file for complete search history.

(56) References Cited

U.S. PATENT DOCUMENTS 7,536,039 B2    5/2009    Shinoda et al.
8,563,970 B2    10/2013   Choi et al.
(Continued)

FOREIGN PATENT DOCUMENTS

JP    4-355720 A    12/1992
KR    10-2006-0003877 A    1/2006
(Continued)

*Primary Examiner* — Edemio Navas, Jr.
(74) *Attorney, Agent, or Firm* — Cha & Reiter, LLC.

(57) ABSTRACT

An electronic device according to various embodiments of the present invention comprises: a display panel; a biometric sensor module disposed on the back surface of the display panel; a processor electrically connected to the display panel and the biometric sensor module, and configured to acquire biometric information by using the biometric sensor module; a first adhesive member filling the gap formed between the back surface of the display panel and the biometric sensor module; and a second adhesive member applied on the first adhesive member, wherein the biometric sensor module can be attached to the back surface of the display panel by using the second adhesive member. In addition, other embodiments are possible.

15 Claims, 15 Drawing Sheets

(56) References Cited

U.S. PATENT DOCUMENTS

| | | |
|---|---|---|
| 8,803,258 B2 | 8/2014 | Gozzini et al. |
| 9,117,401 B2 | 8/2015 | Choi et al. |
| 9,639,224 B2 | 5/2017 | Lee et al. |
| 9,697,409 B2 | 7/2017 | Myers et al. |
| 10,116,868 B2 | 10/2018 | Wyrwas et al. |
| 2006/0034499 A1 | 2/2006 | Shinoda et al. |
| 2010/0097775 A1* | 4/2010 | Kashiwazaki ......... H05K 3/284 |
| | | 361/783 |
| 2011/0254108 A1* | 10/2011 | Gozzini ............. G06K 9/00053 |
| | | 257/415 |
| 2013/0193415 A1 | 8/2013 | Choi et al. |
| 2013/0320851 A1 | 12/2013 | Choi et al. |
| 2013/0323499 A1 | 12/2013 | Choi et al. |
| 2015/0071509 A1 | 3/2015 | Myers |
| 2015/0310251 A1 | 10/2015 | Wyrwas et al. |
| 2015/0363629 A1 | 12/2015 | Lee et al. |
| 2017/0213097 A1* | 7/2017 | Vogel ..................... G06K 9/209 |
| 2018/0239941 A1* | 8/2018 | Mackey ............... G06K 9/0004 |
| 2019/0362060 A1* | 11/2019 | Baek ....................... G06F 21/32 |
| 2019/0384960 A1* | 12/2019 | Kwon ..................... G06F 3/041 |

FOREIGN PATENT DOCUMENTS

| | | |
|---|---|---|
| KR | 10-1366701 B1 | 2/2014 |
| KR | 10-2014-0076338 A | 6/2014 |
| KR | 10-1449226 B1 | 10/2014 |
| KR | 10-2015-0013981 A | 2/2015 |
| KR | 10-2015-0143310 A | 12/2015 |
| KR | 10-2016-0051880 A | 5/2016 |

* cited by examiner

<91>

<92>

<93>

<1001>

<1002>

<1003>

US 10,956,764 B2

ELECTRONIC DEVICE COMPRISING BIOMETRIC SENSOR

CROSS REFERENCE TO RELATED APPLICATIONS

This application is a National Phase Entry of PCT International Application No. PCT/KR2018/004205, which was filed on Apr. 10, 2018, and claims a priority to Korean Patent Application No. 10-2017-0046973, which was filed on Apr. 11, 2017, the contents of which are incorporated herein by reference.

TECHNICAL FIELD

The disclosure relates to a device including a biometric sensor sensing biometric information of a user.

BACKGROUND ART

A technology for performing user authentication using biometric information (e.g., a fingerprint, an iris, or the like) of a user obtained by a biometric sensor has been developed recently. The method of a biometric sensor for fingerprint recognition may be divided into an optical ultrasonic method and an electrostatic method, depending on the method of obtaining fingerprint information.

DISCLOSURE

Technical Problem

An optical sensor needs to maintain a constant distance between a display and a sensor and needs to prevent a foreign object (e.g., dust) from flowing between the display and the sensor. However, the performance of the sensor may be degraded because the distance between the display and the biometric sensor is changed due to external shock or aging while an electronic device is used, or due to the foreign object between the display and the sensor.

Various embodiments of the disclosure may provide a biometric sensor that has a structure for stably maintaining the distance between the display and the sensor and preventing a foreign object from entering between the display and the sensor, and a device including the biometric sensor.

Technical Solution

According to various embodiments of the disclosure, an electronic device may include a display panel and a biometric sensor module disposed on a rear surface of the display panel, a processor electrically connected to the display panel and the biometric sensor module and obtaining biometric information, using the biometric sensor module, a first adhesive member filling a cap formed between the rear surface of the display panel and the biometric sensor module, and a second adhesive member applied on the first adhesive member. The biometric sensor module may be attached to the rear surface of the display panel, using the second adhesive member.

According to various embodiments of the disclosure, a display device may include a display panel, a biometric sensor module disposed on a rear surface of the display panel and sensing biometric information, a first adhesive member filling a cap formed between the rear surface of the display panel and the biometric sensor module, and a second adhesive member applied on the first adhesive member. The biometric sensor module may be attached to the rear surface of the display panel, using the second adhesive member.

Advantageous Effects

According to various embodiments of the disclosure, the performance of the sensor may be prevented from being degraded, by stably maintaining the distance between the display and the sensor and preventing a foreign object from entering between the display and the sensor.

MODE FOR INVENTION

Figure 1:
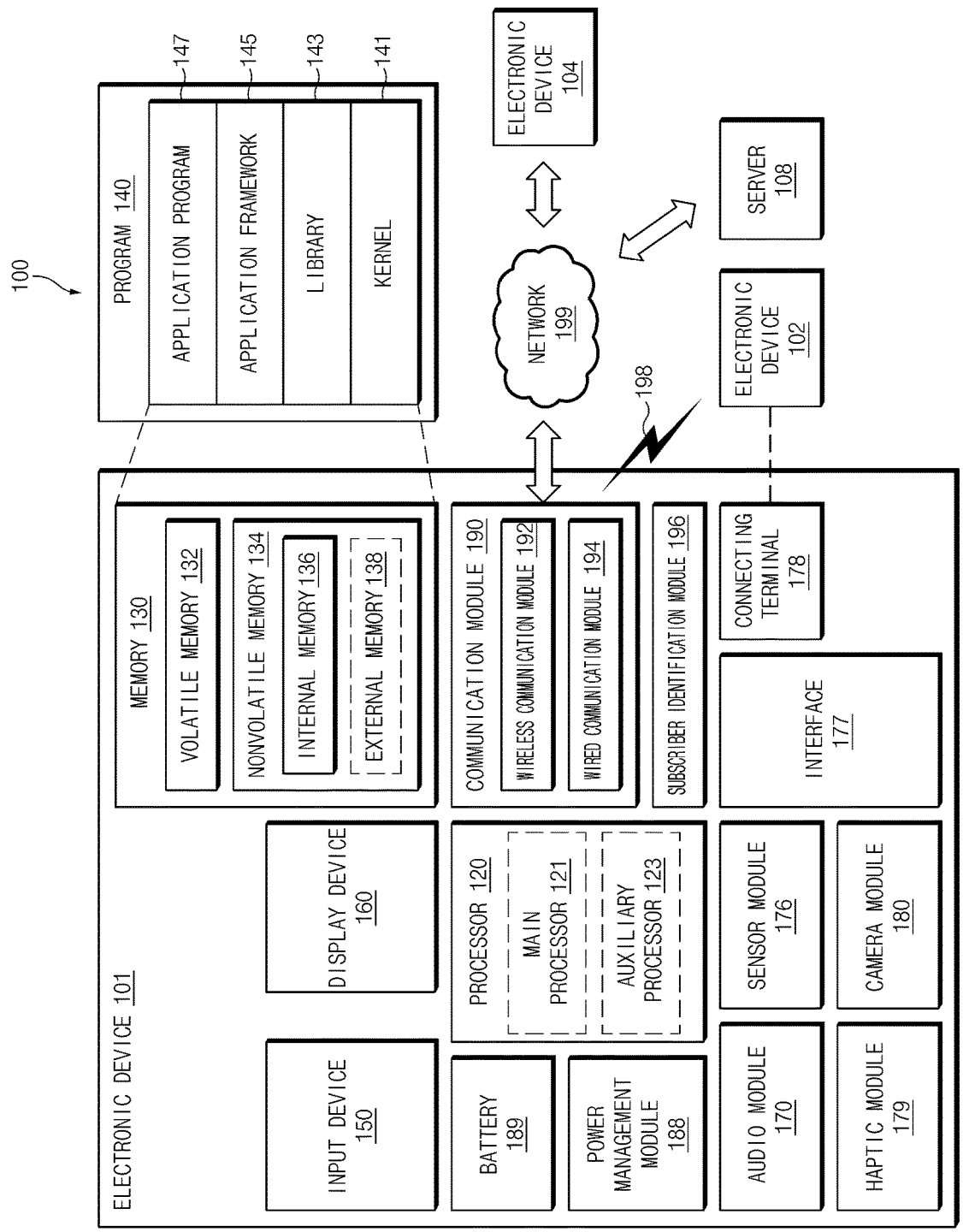
FIG. 1 is a block diagram of an electronic device in a network environment, according to various embodiments.

Hereinafter, various embodiments of the disclosure will be described with reference to accompanying drawings. However, those of ordinary skill in the art will recognize that modification, equivalent, and/or alternative on various embodiments described herein can be variously made without departing from the scope and spirit of the disclosure. With regard to description of drawings, similar components may be marked by similar reference numerals.

FIG. 1 is a block diagram of an electronic device in a network environment, according to various embodiments.

Referring to FIG. 1, an electronic device 101 in a network environment 100 may communicate with an electronic device 102 through a short range wireless communication 198 or may communicate with an electronic device 104 or a server 108 over a network 199. According to an embodiment, the electronic device 101 may communicate with the electronic device 104 through the server 108. According to an embodiment, the electronic device 101 may include a processor 120, a memory 130, an input device 150 (e.g., a microphone or a mouse), a display device 160, an audio module 170, a sensor module 176, an interface 177, a haptic module 179, a camera module 180, a power management module 188, a battery 189, a communication module 190, and a subscriber identification module 196. In any embodiment, the electronic device 101 may not include at least one (e.g., the display device 160 or the camera module 180) of the above-described components or may further include another component. In any embodiment, for example, as in the sensor module 176 (e.g., a fingerprint sensor, an iris sensor, or an illuminance sensor) embedded in the display device 160 (e.g., display), some of components may be implemented integrally.

For example, the processor 120 may operate an operating system or an application program to control at least one other component (e.g., hardware or software component) of the electronic device 101 connected to the processor 120, and may process and calculate various types of data. The processor 120 may load commands or data received from other components (e.g., the sensor module 176 or the communication module 190) into a volatile memory 132, may process the commands or the data, and may store the result data in a nonvolatile memory 134. The processor 120 may include one or more of a central processing unit, an application processor, a graphic processor device, an image signal processor, a sensor hub processor, or a communication processor. According to an embodiment, the processor 120 may include a main processor 121 (e.g., a central processing unit or an application processor) and an auxiliary processor 123 (e.g., a graphic processing unit, an image signal processor, a sensor hub processor, or a communication processor), which is capable of operating independently and which, additionally or alternatively, use lower power than the main processor 121 or is specialized to a specified function. For example, the auxiliary processor 123 may control at least part of the functions or states associated with at least one (e.g., the display device 160, the sensor module 176, or the communication module 190) of the components 130 to 196 of the electronic device 101, instead of the main processor 121 while the main processor 121 is in an inactive (e.g., sleep) state or together with the main processor 121 while the main processor 121 is in an active (e.g., the execution of an application) state. According to an embodiment, the auxiliary processor 123 (e.g., an image signal processor or a communication processor) may be implemented as a part of the operatively associated other components (e.g., the camera module 180 or the communication module 190). According to an embodiment, the processor 120 may be implemented with a system on chip (SoC) or a system in package (SiP).

The memory 130 may store various pieces of data, for example, software (e.g., a program 140) and input data or output data for commands associated with the software, which are used by at least one component (e.g., the processor 120 or the sensor module 176) of the electronic device 101. The memory 130 may include, for example, the volatile memory 132 or the nonvolatile memory 134. For example, the volatile memory 132 may include a random access memory (RAM) (e.g., DRAM, SRAM, or SDRAM). The nonvolatile memory 134 may include, for example, a one-time programmable read-only memory (OTPROM), a programmable read-only memory (PROM), an erasable programmable read-only memory (EPROM), an electrically erasable programmable read-only memory (EEPROM), a mask ROM, a flash ROM, a flash memory, a hard disk drive, or a solid-state drive (SSD). In addition, the nonvolatile memory 134 may be configured in the form of an internal memory 136 or the form of an external memory 138 which is available through connection only if necessary, according to the connection with the electronic device 101. The external memory 138 may include a hard disk, a floppy disk, a magnetic media (e.g., a magnetic tape), an optical media (e.g., a compact disc read only memory (CD-ROM) and a digital versatile disc (DVD)), a magneto-optical media (e.g., a floptical disk), a flash drive, compact flash (CF), secure digital (SD), micro secure digital (Micro-SD), mini secure digital (Mini-SD), extreme digital (xD), a multimedia card (MMC), or a memory stick. The external memory 138 may be operatively or physically connected with the electronic device 101 in a wired manner (e.g., a universal serial bus (USB)) or a wireless (e.g., Bluetooth) manner.

The program 140 may be a software component stored in the memory 130 and may include, for example, a kernel 141, a library 143, an application framework 145 or an application program (interchangeably, "application") 147.

The input device 150 may be a device for receiving commands or data to be used for the component (e.g., the processor 120) of the electronic device 101, from the outside (e.g., a user) of the electronic device 101, and may include, for example, a microphone, a mouse, or a keyboard. According to an embodiment, the keyboard may include a physical keyboard or a virtual keyboard displayed through the display device 160.

The display device 160 may be a device for visually providing information to a user of the electronic device 101 and may include, for example, a display, a hologram device, or a projector, and a control circuit for controlling a corresponding device. The display may include, for example, a liquid crystal display (LCD), a light emitting diode (LED) display, an organic LED (OLED) display, a microelectromechanical systems (MEMS) display, or an electronic paper display. According to an embodiment, the display may be flexibly, transparently, or implemented to be worn on a part of a body. According to an embodiment, the display may include a touch circuitry, which is able to detect a user's input such as a gesture input, a proximity input, or a hovering input or a pressure sensor (interchangeably, a force sensor) which is able to measure the intensity of the pressure by the touch. The touch circuit or the pressure sensor may be implemented integrally with the display or may be implemented with at least one sensor separately from the display. The hologram device may show a stereoscopic image in a space using interference of light. The projector may display an image by projecting light onto a screen positioned inside or outside the electronic device 101.

The audio module 170 may convert a sound and an electric signal in dual directions. According to an embodiment, the audio module 170 may obtain sound through the input device 150 (e.g., a microphone) or may output sound through a sound output device (not illustrated) (e.g., a speaker or a receiver) included in the electronic device 101, or an external electronic device (e.g., the electronic device 102 (e.g., a speaker or a headphone)) wiredly or wirelessly connected to the electronic device 101.

The sensor module 176 may measure or detect an internal operating state (e.g., power or temperature) or an external environment state (e.g., an altitude, a humidity, or brightness) of the electronic device 101 to generate an electrical signal or a data value corresponding to the information of the measured state or the detected state. The sensor module 176 may include, for example, at least one of a gesture sensor, a gyro sensor, a barometric pressure sensor, a magnetic sensor, an acceleration sensor, a grip sensor, a proximity sensor, a color sensor (e.g., a red, green, blue (RGB) sensor), an infrared sensor, a biometric sensor (e.g., an iris sensor, a fingerprint senor, a heartbeat rate monitoring (HRM) sensor, an e-nose sensor, an electromyography (EMG) sensor, an electroencephalogram (EEG) sensor, an electrocardiogram (ECG) sensor), a temperature sensor, a humidity sensor, an illuminance sensor, or an UV sensor. The sensor module 176 may further include a control circuit that controls at least one or more sensors included therein. In any embodiment, the sensor module 176 may be controlled by the main processor 121 (e.g., an application processor), or the auxiliary processor 123 (e.g., a sensor hub processor) that operates independently from the main processor 121. In this case, for example, while the main processor 121 (e.g., an application processor) is in a sleep state, the separate low-power processor may control at least part of the operation or the state of the sensor module 176, without awakening the main processor 121 (e.g., an application processor).

The interface 177 may provide a means for connecting to an external electronic device (e.g., the electronic device 102) depending on a specified standard. According to an embodiment, the interface 177 may include a high definition multimedia interface (HDMI), a universal serial bus (USB) interface, an optical interface, a recommended standard 232 (RS-232) interface, a D-subminiature (D-sub) interface, a mobile high-definition link (MHL) interface, a SD card interface, an multi-media card (MMC) interface, or an audio interface.

A connecting terminal 178 may physically connect the electronic device 101 to an external electronic device (e.g., the electronic device 102). According to an embodiment, the connecting terminal 178 may include, for example, a HDMI connector, an USB connector, an SD card/MMC connector, or an audio connector (e.g., a headphone connector).

The haptic module 179 may convert an electrical signal to a mechanical stimulation (e.g., vibration or movement) or an electrical stimulation which the user may perceive through the sense of touch or the sense of movement. The haptic module 179 may include, for example, a motor, a piezoelectric element, or an electric stimulator.

The camera module 180 may photograph a still image and a video. According to an embodiment, the camera module 180 may include one or more lenses (e.g., a wide-angle lens and a telephoto lens, or a front lens and a rear lens), an image sensor, an image signal processor, or a flash (e.g., a light emitting diode or a xenon lamp).

The power management module 188, which is to manage the power supplied to the electronic device 101, may constitute at least part of a power management integrated circuit (PMIC).

The battery 189 which is a device for supplying a power to at least one component of the electronic device 101 may include, for example, a primary cell incapable of being recharged, a secondary cell rechargeable, or a fuel cell.

The communication module 190 may establish a direct (or wired) communication channel or a wireless communication channel between the electronic device 101 and an external electronic device (e.g., the electronic device 102, the electronic device 104, or the server 108) or may perform communication through the established communication channel. According to an embodiment, the communication module 190 may include a wireless communication module 192 or a wired communication module 194. The communication module 190 may communicate with the external electronic device (e.g., the first external electronic device 102, the second external electronic device 104 or the server 108) through a first network 198 (e.g. a short range communication network such as Bluetooth, Wi-Fi direct, or infrared data association (IrDA)) or a second network 199 (e.g., a long range communication network such as a cellular network, Internet, or a computer network (e.g., LAN or WAN)), using a relevant module among the wireless communication module 192 or the wired communication module 194.

The wireless communication module 192 may support, for example, cellular communication, short-range wireless communication, and global navigation satellite system (GNSS) communication. The cellular communication may include, for example, long-term evolution LTE, LTE Advance LTE-A, code division multiple access CMA, wideband CDMA WCDMA, universal mobile telecommunications system UNITS, wireless broadband WiBro, or global system for mobile communications GSM. The short-range wireless communication may include wireless fidelity Wi-Fi, Wi-Fi Direct, light fidelity Li-Fi, Bluetooth, Bluetooth low energy BLE, ZigBee, near field communication NFC, magnetic secure transmission MST, radio frequency RF, or a body area network BAN. The GNSS may include a global positioning system (GPS), a global navigation satellite system (Glonass), Beidou Navigation Satellite System (hereinafter referred to as "Beidou"), or Galileo, the European global satellite-based navigation system. Hereinafter, in this specification, "GPS" and "GNSS" may be interchangeably used.

According to an embodiment, when the wireless communication module 192 supports cellar communication, the wireless communication module 192 may, for example, identify or authenticate the electronic device 101 within a communication network using the subscriber identification module (e.g., a SIM card) 196. According to an embodiment, the wireless communication module 192 may include a communication processor (CP) operated independently of the processor 120 (e.g., an application processor (AP)). In this case, the communication processor may perform at least part of functions associated with at least one of elements 130 to 196 of the electronic device 101, in substitute for the processor 120 when the processor 120 is in an inactive (sleep) state or together with the processor 120 when the processor 120 is in an active state. According to an embodiment, the wireless communication module 192 may include a plurality of communication modules, each supporting only a relevant communication scheme among cellular communication, short-range wireless communication, or a GNSS communication scheme.

For example, the wired communication module 194 may include a communication processor that supports wired communication such as a local area network (LAN), a power line communication, or a plain old telephone service (POTS).

At least part of the components 120 to 196 may be connected to each other through a communication scheme (e.g., a bus, a general purpose input and output (GPIO), a serial peripheral interface (SPI), or a mobile industry processor interface (MIPI)) between peripheral devices and may exchange signals (e.g., commands or data) with each other.

According to an embodiment, the commands or the data may be transmitted or received between the electronic device 101 and the second external electronic device 104 through the server 108 connected with the second network. Each of the first and second external electronic devices 102 and 104 may be a device of which the type is different from or the same as that of the electronic device 101. According to various embodiments, all or part of operations that the electronic device 101 will perform may be executed by another or plural external electronic devices (e.g., the electronic devices 102 and 104 or the server 108). According to an embodiment, in the case that the electronic device 101 executes any function or service automatically or in response to a request, the electronic device 101 may not perform the function or the service internally, but may alternatively or additionally transmit requests for at least part of a function associated with the electronic device 101 to any other device (e.g., the electronic device 102 or 104 or the server 108). The other electronic device (e.g., the electronic device 102 or 104 or the server 108) receiving the request may execute the requested function or additional function and may transmit the execution result to the electronic device 101. The electronic device 101 may provide the requested function or service using the received result or may additionally process the received result to provide the requested function or service. To this end, for example, cloud computing, distributed computing, or client-server computing may be used.

Figure 2:
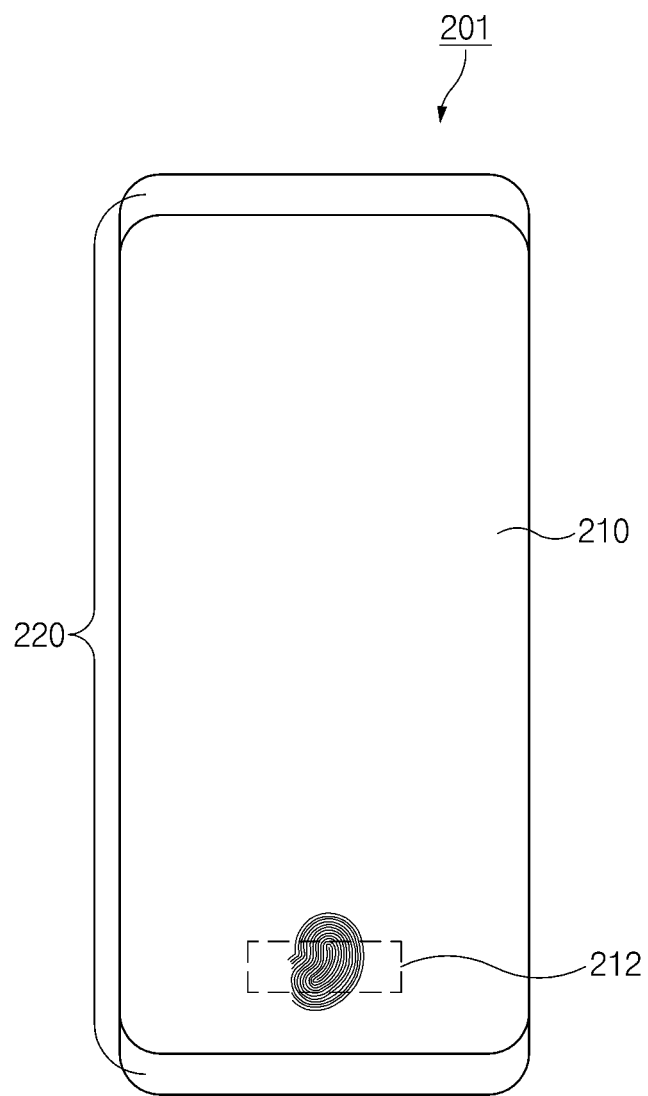
FIG. 2 illustrates an appearance of an electronic device according to an embodiment.

FIG. 2 illustrates an appearance of an electronic device according to an embodiment;

Referring to FIG. 2, a display (or a display panel) 210 and housing 220 may be exposed on the front surface of an electronic device 201 according to an embodiment. According to an embodiment, the electronic device 201 may include various hardware modules not illustrated. For example, a pressure sensor sensing the strength (or pressure) of the touch input of a user and/or a biometric sensor sensing the fingerprint of the user may be disposed on the rear surface of the display 210.

According to an embodiment, the electronic device 201 may detect the fingerprint of the user through a second area 212 of the display 210. To this end, the biometric sensor for sensing the fingerprint may be disposed on the rear surface of the second area 212 in the display 210.

According to various embodiments of the disclosure, even though the biometric sensor is disposed on the rear surface of the display 210, the biometric sensor may accurately obtain the fingerprint information of the user while maintaining the proper distance from the display 210 and may provide a sensor package structure capable of preventing the deterioration in performance due to the inflow of external foreign object into the biometric sensor.

In FIG. 2, the electronic device 201 is exemplary and is not limited to the described example. For example, a receiver, a camera module, an iris sensor, other biometric sensors, or the like may be disposed on the rear surface of the display 210.

Figure 3:
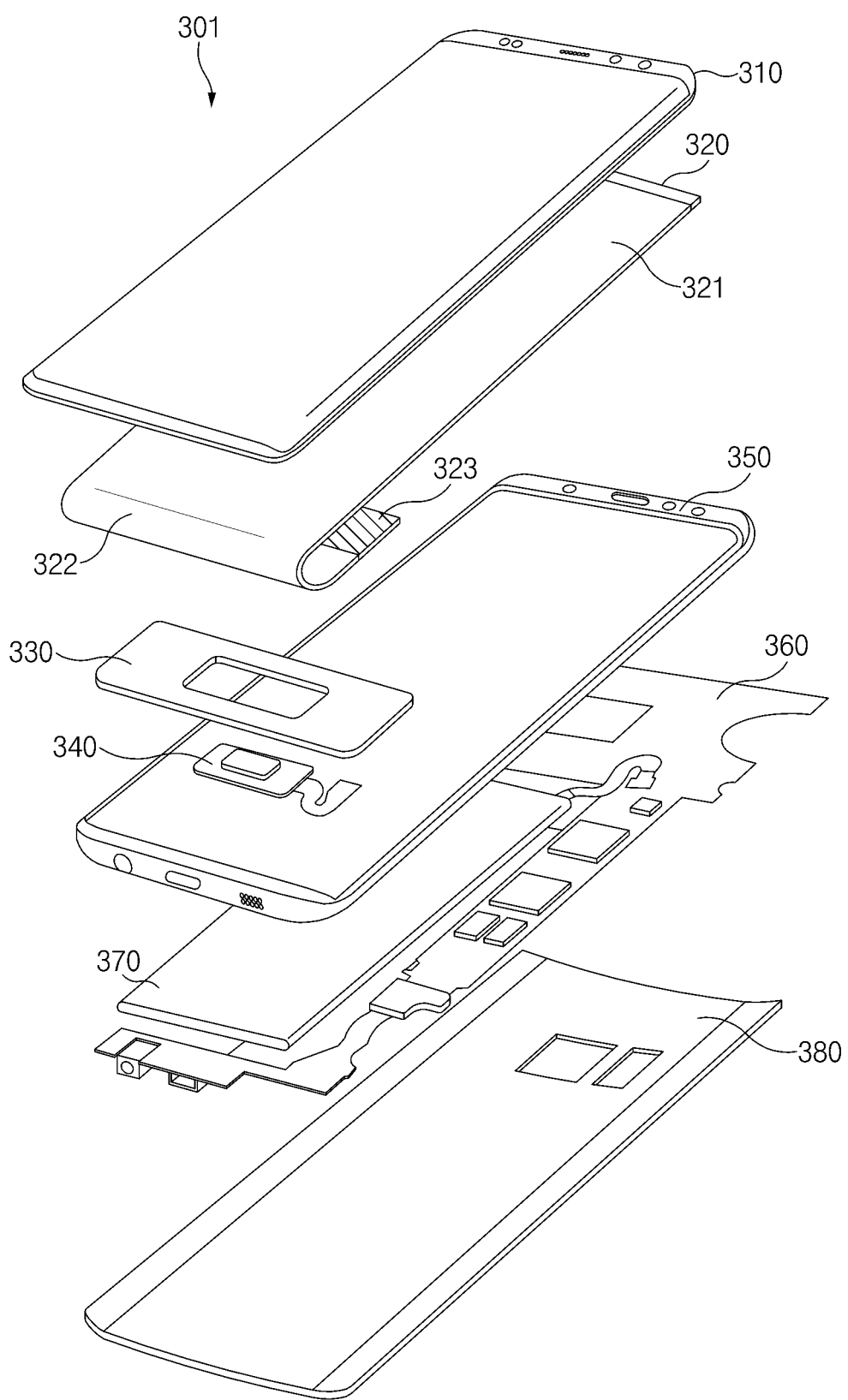
FIG. 3 illustrates an exploded perspective view of an electronic device, according to an embodiment.

FIG. 3 illustrates an exploded perspective view of an electronic device, according to an embodiment.

Referring to FIG. 3, an electronic device 301 (e.g., the electronic device 201) according to an embodiment may include a cover glass 310, a display (or a display panel) 320 (e.g., the display 210), a pressure sensor 330, a biometric sensor module 340 (e.g., a fingerprint sensor), housing 350 (e.g., the housing 220), a circuit board 360, a battery 370, and a rear cover 380. According to various embodiments, the electronic device 301 may be implemented without some of the elements illustrated in FIG. 3 or may be implemented to further include one or more elements not illustrated in FIG. 3.

The cover glass 310 may transmit light generated by the display 320. Furthermore, a user may touch the cover glass 310 by using a portion (e.g., a finger) of his/her body to perform a touch (including a contact using an electronic pen). The cover glass 310 may be formed of, for example, tempered glass, reinforced plastic, a flexible polymer material, or the like and may protect the display 320 or each element included in the electronic device 301 from an external shock. According to various embodiments, the cover glass 310 may be also referred to as a "glass window".

The display 320 may be disposed or coupled below the cover glass 310 so as to be exposed through at least part of the cover glass 310. The display 320 may output content (e.g., a text, an image, a video, an icon, a widget, or a symbol) or may receive a touch input or an electronic pen input from a user.

According to an embodiment, the display 320 may include a display panel, a touch sensor, and/or an electronic pen sensor. For example, the display panel may include a liquid crystal display (LCD) panel, a light-emitting diode (LED) display panel, an organic LED (OLED) display panel, a microelectromechanical systems (MEMS) display panel, or an electronic paper display panel. The touch sensor may include a capacitive touch panel, a pressure sensitive touch panel, a resistive touch panel, an infrared touch panel, or an ultrasonic touch panel. The touch sensor may be inserted between display panels (a so-called "add-on touch panel"), may be formed directly on the display panel (a so-called "on-cell touch panel"), or may be included within the display panel (a so-called "in-cell touch panel"). The electronic pen sensor (e.g., digitizer) may detect a touch, a gesture, hovering, or the like from the electronic pen.

According to an embodiment, the display 320 may include a planar area 321 and a bending area 322 that extends from one side (e.g., an upper side, a lower side, a left side, a right side) of the planar area 321. The pixels (e.g., OLED or the like) of a display panel, the conductive pattern of a touch sensor, and/or the conductive pattern of an electronic pen sensor may be disposed in the planar area 321. The bending area 322 may be electrically connected to a FPCB 323 positioned on the rear surface of the display 320, through various conductive patterns (wires)

According to an embodiment, a part of the bending area 322 may be folded toward the rear surface of the planar area 321. According to various embodiments, the wire of the FPCB 323 may be electrically connected to the circuit board 360 through a specified connector. According to various embodiments, similarly to the planar area 321, pixels for displaying various pieces of information may be disposed in the bending area 322 depending on the design of the electronic device 301.

The pressure sensor 330 may be disposed or coupled below the display 320. For example, the pressure sensor 330 may be interposed between the planar area 321 and the FPCB 323 of the display 320. The pressure sensor 330 may detect or sense pressure (or force) of the outside (e.g., the finger of the user) against the cover glass 310. According to an embodiment, the pressure sensor 330 may include a plurality of electrodes and a dielectric layer. For example, the pressure sensor 330 may sense the pressure of the touch based on a capacitance between the first electrode and the second electrode, which varies with the touch of the user.

The biometric sensor module 340 (e.g., a fingerprint sensor) may be disposed or coupled below the display 320. For example, the biometric sensor module 340 may be attached to the planar area 321 of the display 320. According to an embodiment, the pressure sensor 330 may include a sensor-positioned area (or opening), through which the front and rear surfaces are passed to arrange the biometric sensor module 340. The biometric sensor module 340 may be inserted inside the sensor-positioned area of the pressure sensor 330 so as to be disposed in parallel with the pressure sensor 330.

The biometric sensor module 340 may sense the biometric information (e.g., fingerprint information) of the user. For example, the biometric sensor module 340 may include an optical biometric sensor. For example, the biometric sensor module 340 may capture the fingerprint image of the user, using an embedded image sensor (e.g., a complementary metal oxide semiconductor (CMOS) image sensor or a charge-coupled device (CCD) image sensor). The unique fingerprint minutiae of a fingerprint may be extracted from the fingerprint image, and the fingerprint minutiae may be used for user authentication by comparing the fingerprint minutiae with the pre-registered fingerprint minutiae.

The biometric sensor module 340 may obtain fingerprint information by receiving at least part (e.g., light reflected by the user's finger, or the like) of light output from at least one light emitting element included in the display 320. According to various embodiments, the biometric sensor module 340 may include a light emitting unit and a light receiving unit; the biometric sensor module 340 may obtain the fingerprint information by outputting light using the light emitting unit and then receiving the light reflected by an external object (e.g., a finger).

The housing 350 may form at least part of the appearance of the electronic device 301 and may accommodate each component included in the electronic device 301. For example, the housing 350 may form the appearance of the side surface (e.g., an upper side surface, a lower side surface, a left side surface, and/or a right side surface) of the electronic device 301. According to various embodiments, the housing 350 may include pieces of housing. The housing 350 may be referred to as a rear case, a rear plate, or the like. According to an embodiment, at least part of side surfaces of the housing 350 may be formed of a metal material so as to be used as an antenna structure.

According to an embodiment, the housing 350 may include a bracket. The bracket may be formed of, for example, magnesium alloy and may be disposed under the display 320 and on the circuit board 360. The bracket may be coupled with the display 320 and the circuit board 360 to support the display 320 and the circuit board 360 physically.

According to an embodiment, the circuit board 360 may be disposed under the housing 350 (or on the housing 350). Various types of electronic parts, elements, printed circuits, or the like (e.g., a processor, a memory, a communication circuit, or the like) of the electronic device 301 may be mounted or arranged on the circuit board 360. According to various embodiments, the circuit board 360 may be referred to as a "main board" or "printed board assembly (PBA)" or may be simply referred to as a "PCB". The circuit board 360 may include, for example, a main circuit board or a sub circuit board. According to an embodiment, the main circuit board and the sub circuit board may be electrically connected to each other through a specified connector or a specified wire. For example, the circuit board 360 may be implemented with a rigid printed circuit board (PCB) and/or FPCB.

The battery 370 may convert chemical energy and electrical energy bidirectionally. For example, the battery 370 may convert chemical energy into electrical energy and may supply the converted electrical energy to the display 320, the pressure sensor 330, the biometric sensor module 340 and various components or modules connected to the circuit board 360. According to an embodiment, a power management module (e.g., a power management integrated circuit (PMIC)) for managing charging and discharging of the battery 370 may be included in the circuit board 360.

The rear cover 380 may be coupled with the rear surface of the electronic device 301. The rear cover 380 may be formed of tempered glass, a plastic injection-molding material, and/or metal. According to various embodiments, the rear cover 380 may be integrated with the housing 350 or may be implemented to be detachable by the user.

Figure 4A:
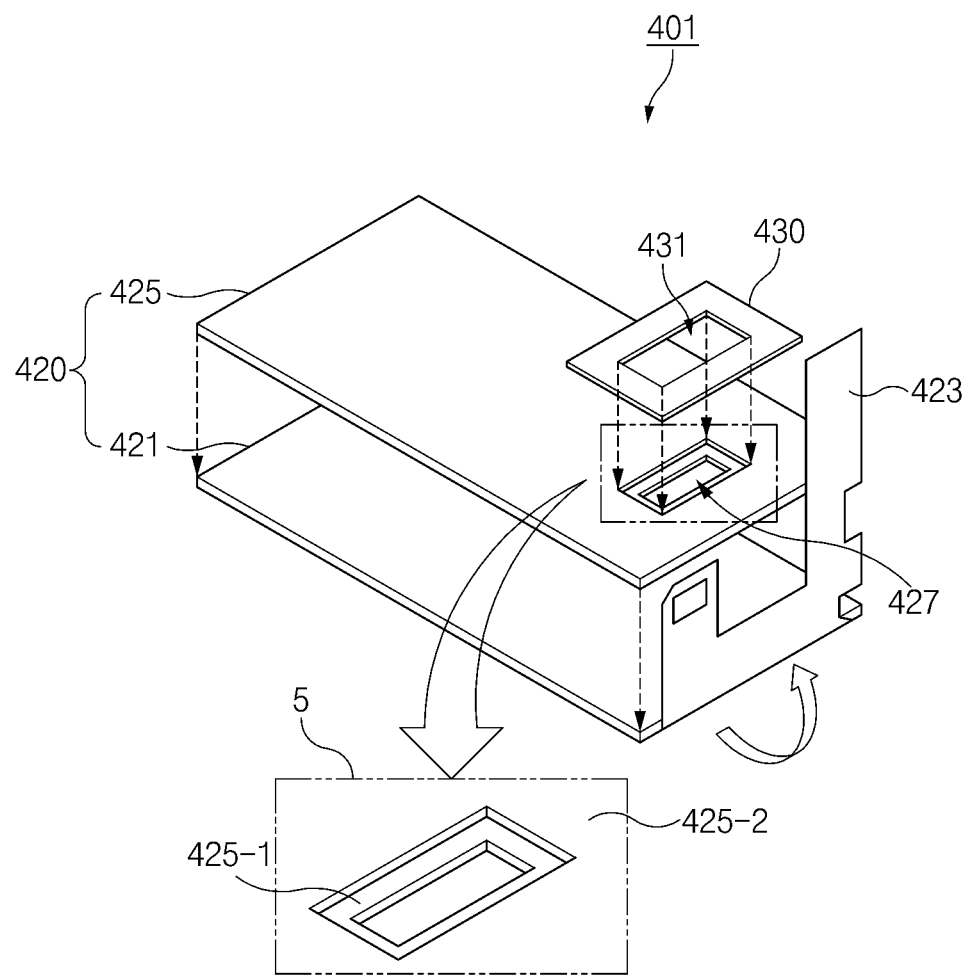
FIGS. 4A and 4B illustrate coupling structures of an electronic device, according to an embodiment.
Figure 4B:
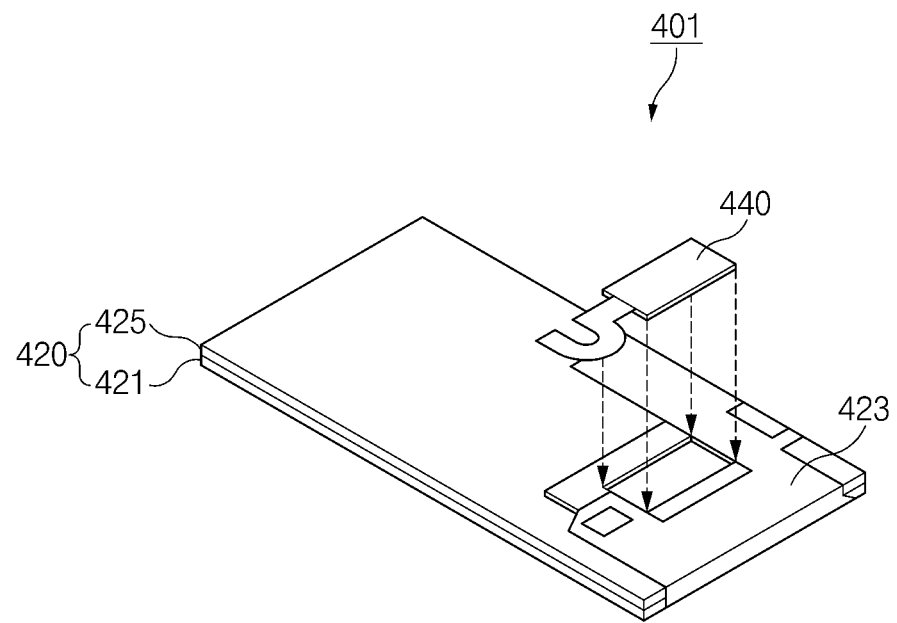

FIGS. 4A and 4B illustrate coupling structures of an electronic device, according to an embodiment.

For example, FIGS. 4A and 4B illustrate perspective views when the rear surface of an electronic device 401 is viewed.

Referring to FIG. 4A, according to an embodiment, the electronic device 401 (e.g., the electronic device 301 of FIG. 3) may include a display (or a display panel) 420 (e.g., the display 320 of FIG. 3) and a pressure sensor 430 (e.g., the pressure sensor 330 of FIG. 3). Referring to FIG. 4B, according to an embodiment, the electronic device 401 (e.g., the electronic device 301 of FIG. 3) may further include a biometric sensor module 440 (e.g., the biometric sensor module 340 of FIG. 3).

According to an embodiment, the display 420 may include a panel layer (e.g., a display panel) 421 and a layer 425. According to an embodiment, the panel layer 421 may include at least one emitting element. According to an embodiment, the panel layer 421 may include at least one hole. For example, the panel layer 421 may include at least one cap between a plurality of pixels. The reflected light reflected by the user's finger after being outputted from the panel layer 421 may pass through at least one hole included in the panel layer 421 and then may reach the biometric sensor module 440. According to an embodiment, the layer 425 may be disposed to face the rear surface of the panel layer 421. According to an embodiment, the layer 425 may include a sensor-positioned area 427 for accommodating a biometric sensor module (e.g., the biometric sensor module 340 of FIG. 3). The sensor-positioned area 427 may be the form through which the front surface and rear surface are passed, so as to face the partial area of the panel layer 421 in a state where a biometric sensor module is inserted.

Referring to an image 5 obtained by enlarging a partial area 3 of the layer 425, the layer 425 may include a first layer 425-1 and a second layer 425-2. According to an embodiment, the size of a penetration area (or opening) formed on each of the first layer 425-1 and the second layer 425-2 may be different from each other. For example, the area size of the penetration area of the second layer 425-2 may be greater than the area size of the penetration area of the first layer 425-1.

According to an embodiment, the display 420 may include a circuit board 423 (e.g., the FPCB 323 of FIG. 3) on which a display IC and/or a touch sensor IC is disposed. According to an embodiment, the circuit board 423 may extend from the one side surface (e.g., a lower side surface) of the panel layer 421 and may be electrically connected to the panel layer 421.

According to an embodiment, the pressure sensor 430 may include a sensor-positioned area 431 for accommodating the biometric sensor module 340. The sensor-positioned area 431 of the pressure sensor 430 may be the form through which the front surface and rear surface are passed, so as to face the partial area of the panel layer 421 in a state where a biometric sensor module is inserted. According to an embodiment, the area size of the sensor-positioned area 431 of the pressure sensor 430 may be greater than or equal to the area size of the sensor-positioned area 427 of the layer 425.

According to an embodiment, the circuit board 423 may be folded in the direction of the rear surface of the layer 425 to overlap with the layer 425 and at least part of the pressure sensor 430 and may be attached to the layer 425 and the pressure sensor 430.

Referring to FIG. 4B, the biometric sensor module 440 (e.g., the biometric sensor module 340 of FIG. 3) may be attached to the rear surface of the display 420. For example, one surface of the biometric sensor module 440 may pass through the pressure sensor 430 and the second layer 425-2 of the layer 425 and may be attached to the first layer 425-1 of the layer 425.

Figure 5:
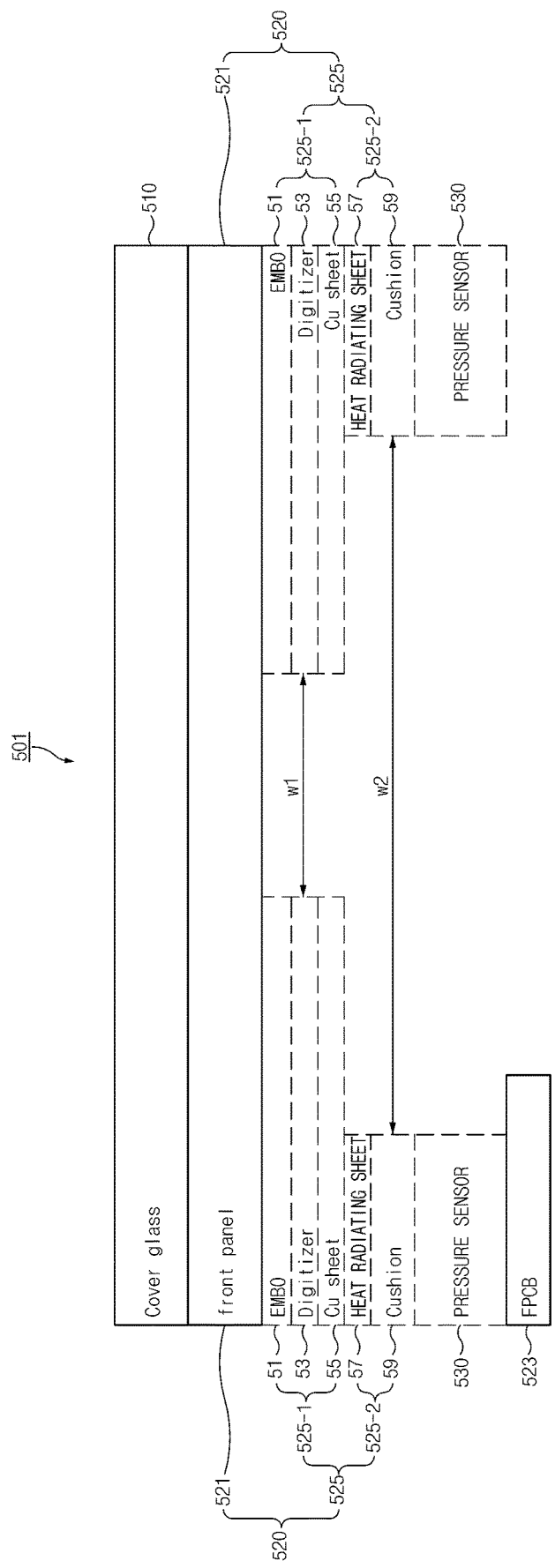
FIG. 5 illustrates a sectional view of the electronic device according to an embodiment.

FIG. 5 illustrates a sectional view of the electronic device according to an embodiment;

The sectional view illustrated in FIG. 5 corresponds to a sectional view in a state where a biometric sensor module (e.g., the biometric sensor module 340 of FIG. 3) is not attached to a display 520. Referring to FIG. 5, an electronic device 501 (e.g., the electronic device 301 of FIG. 3) may include a cover glass 510 (e.g., the cover glass 310 of FIG. 3), a display (or a display panel) 520 (e.g., the display 320 of FIG. 3), and a pressure sensor 530 (e.g., the pressure sensor 330 of FIG. 3).

The cover glass 510 may be positioned on the top layer of the electronic device 501. The display 520 may be disposed under the cover glass. The display 520 may include a panel layer 521 (e.g., the panel layer 421) and a layer 525 (e.g., the layer 425). According to an embodiment, the panel layer 521 may include at least one emitting element and may be disposed under the cover glass 510. According to an embodiment, the layer 525 may be disposed under the panel layer 521. According to an embodiment, the layer 525 may include a first layer 525-1 (e.g., the first layer 425-1) and a second layer 525-2 (e.g., the second layer 425-2). For example, the first layer 525-1 may include a support member 51 in which a pattern is formed, a digitizer (or an electronic pen sensor) 53 receiving an input from an electronic pen, and a metal layer 55 (e.g., a copper layer). The support member 51 may absorb external impact to the panel layer 521, may improve the optical characteristics, and may visually obscure the pattern included in the digitizer 53. For example, the second layer 525-2 may include a heat radiating layer 57 for performing a heat radiating function and a cushion layer 59 for absorbing external impact. The stacked structure of the first layer 525-1 and second layer 525-2 illustrated in FIG. 5 is exemplary. The layer 525 may not include a part of the plurality of layers illustrated in FIG. 5, may further include at least another layer, or may be disposed after the location of at least part of a plurality of layers is changed. For example, the layer 525 may not include the digitizer 53 and the metal layer 55, which are illustrated in FIG. 5. For another example, the layer 525 may not include the support member 51 and a heat radiating sheet 57.

According to an embodiment, the size of a penetration area (or opening) formed on each of the first layer 525-1 and the second layer 525-2 may be different from each other. For example, the width w2 of the penetration area of the second layer 525-2 may be greater than the width w1 of the penetration area of the first layer 525-1. As such, the layer 525 may form a step structure by the first layer 525-1 and the second layer 525-2.

According to an embodiment, the pressure sensor 530 may be disposed under the layer 525. According to an embodiment, a circuit board 523 may be disposed under the pressure sensor 530. For example, as described with reference to FIG. 4, the circuit board 523 may extend from the one side surface of the display 520 (e.g., the panel layer 521), may be folded in the rear surface direction of the layer 525, and may be attached to the pressure sensor 530. According to an embodiment, the electronic device 501 may not include the pressure sensor 530.

Figure 6:
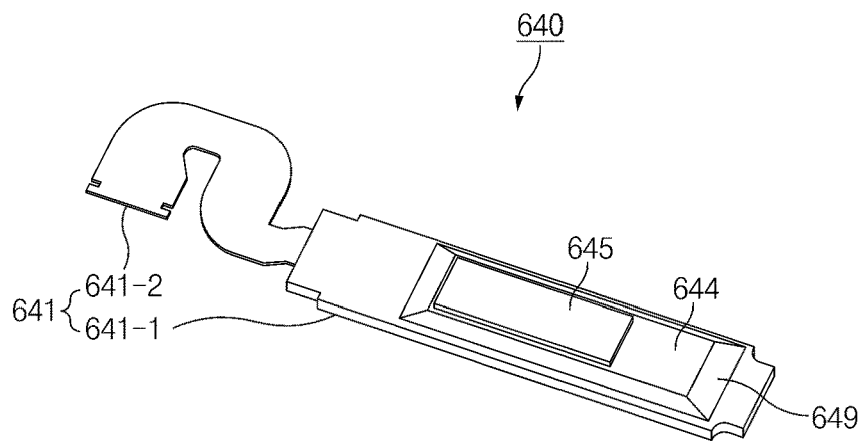
FIG. 6 illustrates a package structure of a biometric sensor module, according to an embodiment.
Figure 6:
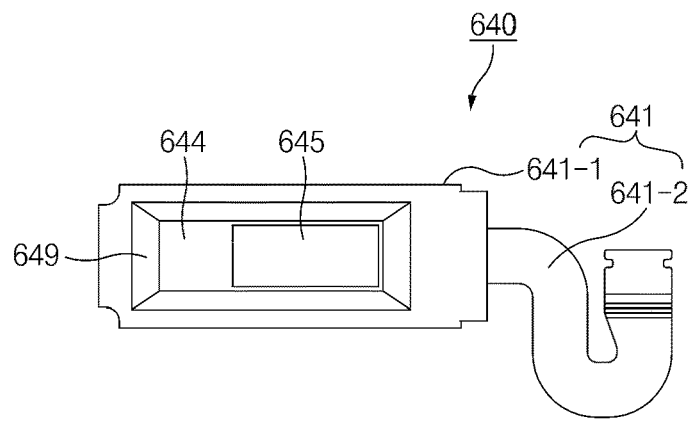
Figure 6:
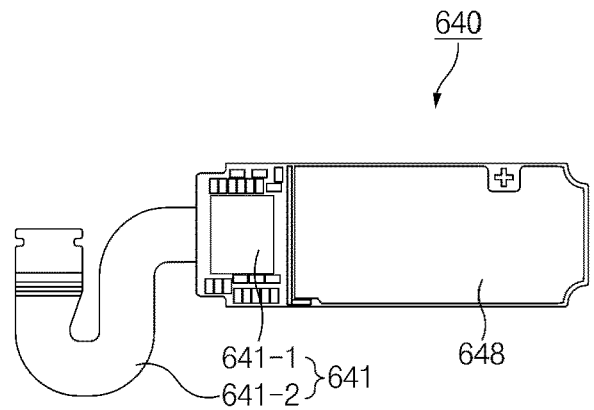

FIG. 6 illustrates a package structure of a biometric sensor module, according to an embodiment.

<61> image of FIG. 6 illustrates an example of the perspective view of a biometric sensor module (e.g., a fingerprint sensor) 640 (e.g., the biometric sensor module 340 of FIG. 3); <62> image illustrates an example of the front view of the biometric sensor module 640; <63> image illustrates an example of the rear view of the biometric sensor module 640.

Referring to FIG. 6, the biometric sensor module 640 may include a circuit board 641, an optical layer 644, an optical filter layer 645, a magnetic screen layer 648 (e.g., magnetic metal powder sheet) and a protection member 649. According to various embodiments, the biometric sensor module 640 may be implemented without some of the elements illustrated in FIG. 6 or may be implemented to further include one or more elements not illustrated in FIG. 6. For example, an image sensor (e.g., an image sensor 743) for obtaining fingerprint information and/or a conductive wire (e.g., a conductive wire 747) electrically connecting the circuit board 641 to an image sensor may be included between the circuit board 641 and the optical layer 644.

According to an embodiment, the circuit board 641 may include a rigid printed circuit board (RPCB) 641-1 and a flexible printed circuit board (FPCB) 641-2. The RPCB 641-1 may include a passive element, a printed circuit, and a sensor IC for controlling a biometric sensor. For example, the passive element, the printed circuit, and the sensor IC may be disposed on the rear surface of the RPCB 641-1. The FPCB 641-2 may extend from one side surface of the RPCB 641-1. The FPCB 641-2 (or a connecting part) may be electrically connected to another circuit board (e.g., the circuit board 423 of FIG. 4A) in a state where the FPCB 641-2 is attached to a display (e.g., the display 420 of FIG. 4A).

According to an embodiment, the optical layer 644 may be disposed on the circuit board 641. For example, the optical layer 644 may be disposed on an image sensor disposed on the circuit board 641. For example, the optical layer 644 may improve the optical characteristics of the reflected light reflected by an external object (e.g., finger) and may improve the light receiving efficiency of the image sensor by refracting the reflected light.

According to an embodiment, the optical filter layer 645 may be disposed on the optical layer 644. According to an embodiment, the optical filter layer 645 may be disposed on at least a partial area of the optical layer 644. For example, the optical filter layer 645 may transmit only the light of a specific wavelength (e.g., visible light) among the reflected light reflected by an external object (e.g., a finger). For example, the optical filter layer 645 may transmit only the light (e.g., green light) of a wavelength required by the image sensor (e.g., an image sensor 743) to obtain the fingerprint information or a wavelength capable of passing through a hole formed in the panel layer (e.g., the panel layer 421 of FIG. 4A) of a display. According to an embodiment, the optical filter layer 645 may include a poly ethylene terephthalate (PET) film.

According to an embodiment, the magnetic screen layer 648 may be attached to one surface (e.g., a rear surface) of the circuit board 641. For example, the magnetic screen layer 648 may include magnetic powder and/or metal powder. As the magnetic screen layer 648 forms a sensor-positioned area on the layer (e.g., the layer 425 of FIG. 4A)

of a display, a hole may be generated in the partial area of a digitizer included in the layer. The magnetic screen layer 648 may compensate for the change in the magnetic field caused by a hole formed on the layer, thereby preventing the performance deterioration of the digitizer. When the layer does not include the digitizer, the magnetic screen layer 648 may be omitted.

According to an embodiment, the protection member 649 may be disposed on the circuit board 641 to cover at least a partial area of the circuit board 641. The protection member 649 may have a structure tilted such that the height of the protection member 649 decreases as it goes towards the periphery of the biometric sensor module 640. For example, as the protection member 649 approaches an optical layer 644, the height of the protection member 649 may increase; as the protection member 649 is far from the optical layer 644, the height of the protection member 649 may decrease.

According to an embodiment, the protection member 649 may fix a conductive wire and may protect the conductive wire from the outside, by surrounding the conductive wire (e.g., the conductive wire 747 of FIG. 7A or 7B) for electrically connecting the circuit board 641 to the image sensor. The conductive wire may be completely blocked from the outside by the protection member 649. For example, the protection member 649 may include epoxy resin or silicone.

Figure 7A:
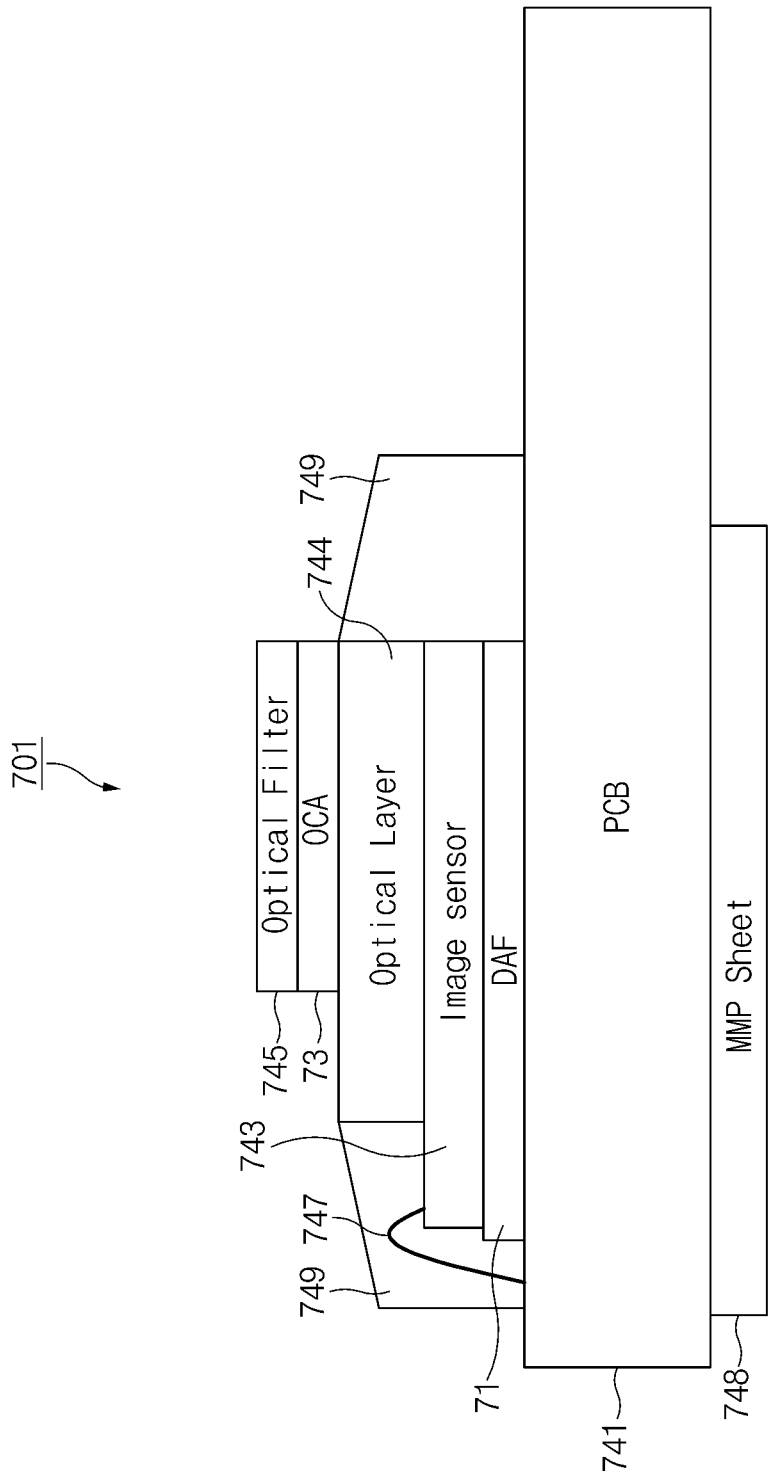
FIG. 7A illustrates a sectional view of a biometric sensor module, according to an embodiment.

FIG. 7A illustrates a sectional view of a biometric sensor module, according to an embodiment.

Referring to FIG. 7A, a biometric sensor module 701 (e.g., the biometric sensor module 640 of FIG. 6) may include a circuit board 741 (e.g., the circuit board 641), the image sensor (or an image sensor array) 743, an optical layer 744 (e.g., the optical layer 644), an optical filter layer 745 (e.g., the optical filter layer 645), the conductive wire 747, a magnetic screen layer 748 (e.g., the magnetic screen layer 648), and a protection member 749 (e.g., the protection member 649)

According to an embodiment, the image sensor 743 may be disposed on the circuit board 741. For example, the image sensor 743 may be attached to the circuit board 741 by a first adhesive film (e.g., a die adhesive film (DAF)) 71. For example, the image sensor 743 may be an array-typed image sensor in which a plurality of image sensors are disposed at a specified interval. The image sensor 743 may obtain fingerprint information (or fingerprint image) using the reflected light reflected by the user's finger.

According to an embodiment, the optical filter layer 745 may be disposed on at least a partial area of the optical layer 744. For example, the optical filter layer 745 may be attached to the optical layer 744 by a second adhesive film (e.g., an optically clear adhesive (OCA) film, an optically clear resin (OCR) film, or a die attached film (DAF)) 73. The second adhesive film 73 may be transparent to ensure optical characteristics.

According to an embodiment, the conductive wire 747 may connect the circuit board 741 to the image sensor 743. For example, the conductive wire 747 may include a plurality of wires connecting the circuit board 741 to the image sensor 743. The fingerprint information obtained by the image sensor 743 may be transmitted to a sensor IC disposed on the circuit board 741, through the conductive wire 747.

According to an embodiment, the protection member 749 may be disposed on the side surface of the image sensor 743 and the optical layer 744 on the circuit board 741 to fix the image sensor and the optical layer 744 and to protect the image sensor and the optical layer 744 from the outside. According to an embodiment, the protection member 749 may be formed to surround the conductive wire 747 to fix the conductive wire 747 and to protect the conductive wire 747 from the outside. The conductive wire 747 may be completely blocked from the outside by the protection member 749. For example, the protection member 749 may include silicone.

Figure 7B:
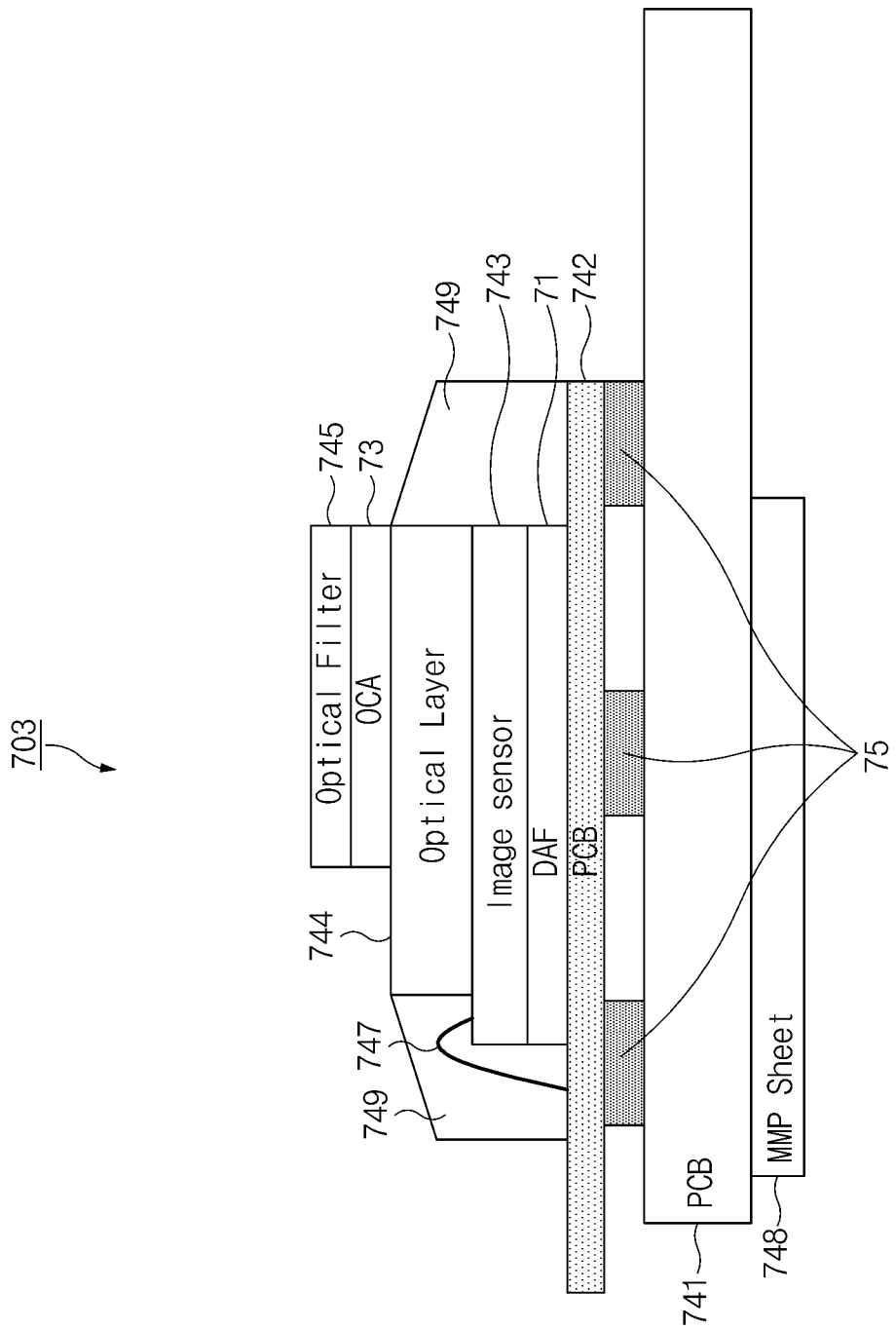
FIG. 7B illustrates a sectional view of a biometric sensor module, according to an embodiment.

FIG. 7B illustrates a sectional view of a biometric sensor module, according to an embodiment.

Referring to FIG. 7B, a biometric sensor module 703 (e.g., the biometric sensor module 640 of FIG. 6) may include the main circuit board 741 (e.g., the circuit board 641 of FIG. 6), a sub circuit board 742, the image sensor (or an image sensor array) 743, the optical layer 744, the optical filter layer 745, the conductive wire 747, the magnetic screen layer 748, and the protection member 749.

According to an embodiment, the sub circuit board 742 may be disposed on the main circuit board 741. For example, the sub circuit board 742 may be attached to the main circuit board 741 by at least one third adhesive film 75. According to an embodiment, the third adhesive film 75 may include, for example, a conductive material, and may connect the main circuit board 741 to the sub circuit board 742. For example, the third adhesive film 75 may include conductive epoxy or solder.

According to an embodiment, the image sensor 743 may be disposed on the sub circuit board 742. For example, the image sensor 743 may be attached to the sub circuit board 742 by the first adhesive film (e.g., a DAF) 71.

According to an embodiment, the protection member 749 may be disposed on the side surface of the image sensor 743 and the optical layer 744 on the sub circuit board 742 to fix the image sensor and the optical layer 744 and to protect the image sensor and the optical layer 744 from the outside.

According to an embodiment described with FIGS. 7A and 7B, an embodiment is exemplified as the biometric sensor module is formed on a separate circuit board (e.g., the circuit board 741) distinguished from another component. However, the biometric sensor module may be formed on another circuit board (i.e., another circuit board (e.g., the FPCB 323 of FIG. 3) illustrated in FIG. 3).

Figure 7C:
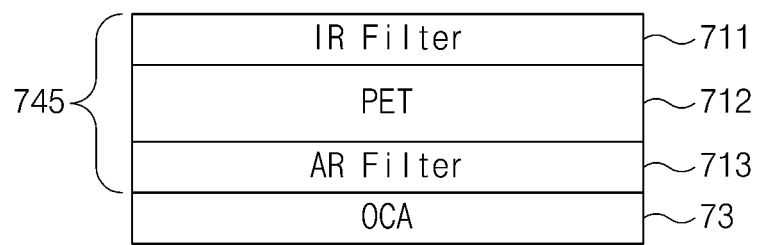
FIG. 7C is a sectional view of an optical filter layer, according to an embodiment.

FIG. 7C is a sectional view of an optical filter layer, according to an embodiment.

Referring to FIG. 7C, the optical filter layer 745 may include a first filter layer (e.g., IR filter layer) 711, a poly ethylene terephthalate (PET) layer 712, and a second filter layer (e.g., an anti-reflection (AR) filter layer) 713.

According to an embodiment, the first filter layer 711 may block the light of a specific wavelength (e.g., infrared light). For example, the first filter layer 711 may include an infrared cut-off filter. According to an embodiment, the second filter layer 713 may include an anti-reflection film for preventing the light-receiving efficiency from lowering as the reflected light reflected by the user's body (e.g., finger) is reflected.

According to an embodiment, the first filter layer 711 and the second filter layer 713 may be attached to the PET layer 712. For example, the first filter layer 711 may be attached on the PET layer 712, and the second filter layer 713 may be attached under the PET layer 712. According to an embodiment, the optical filter layer 745 may not include a part of the first filter layer 711 and the second filter layer 713. According to an embodiment, the locations of the first filter layer 711 and the second filter layer 713 may be changed to each other.

According to an embodiment, the optical filter layer 745 may be attached to an optical layer (e.g., the optical layer 744 of FIG. 7A or 7B) by the second adhesive film 73 (e.g., an OCA film, an OCR film or a DAF).

Figure 8:
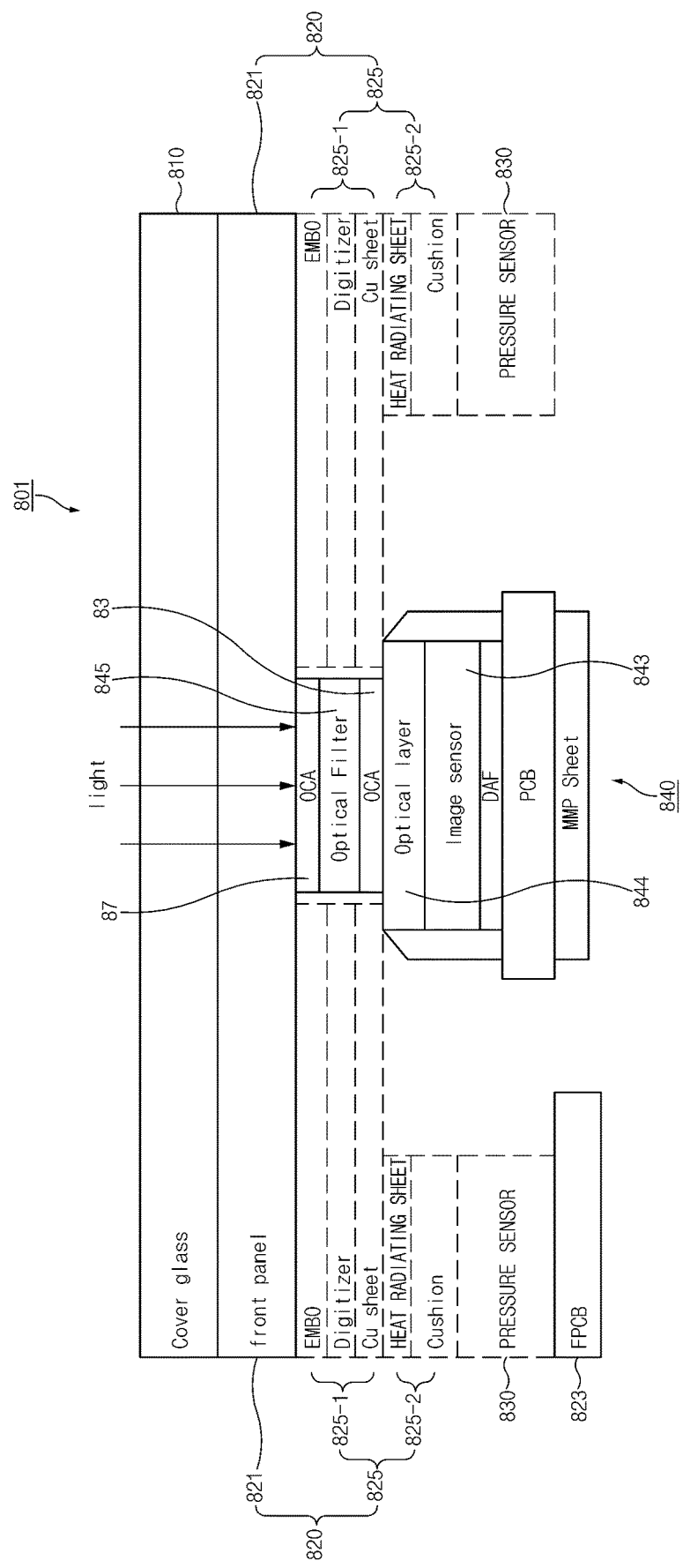
FIG. 8 is a sectional view of an electronic device, according to an embodiment.

FIG. 8 is a sectional view of an electronic device, according to an embodiment.

The sectional view illustrated in FIG. 8 corresponds to a sectional view in a state where a biometric sensor module 840 is attached to a display 820. Referring to FIG. 8, an electronic device 801 (e.g., the electronic device 301 of FIG. 3) may include a cover glass 810 (e.g., the cover glass 310 of FIG. 3), the display (or a display panel) 820 (e.g., the display 320 of FIG. 3), a pressure sensor 830 (e.g., the pressure sensor 330 of FIG. 3), and the biometric sensor module 840 (e.g., the biometric sensor module 340 of FIG. 3).

According to an embodiment, the biometric sensor module 840 may pass through the sensor-positioned area (e.g., the sensor-positioned area 427 of FIG. 4A) formed on the display 820 and the sensor-positioned area (e.g., the sensor-positioned area 431 of FIG. 4A) formed on the pressure sensor 830 to be attached to the rear surface of the display 820. For example, an optical filter layer 845 of the biometric sensor module 840 may be attached to one surface (e.g., a rear surface) of a panel layer 821 by a fourth adhesive film (e.g., an OCA film, an OCR, or a DAF) 87 interposed between the optical filter layer 845 and the panel layer 821 (e.g., the panel layer 421). The fourth adhesive film 87 may be transparent to ensure optical characteristics.

According to an embodiment, in a state where the biometric sensor module 840 is attached to the display 820, the biometric sensor module (e.g., an image sensor 843, an optical layer 844, and an optical filter layer 845) may face the panel layer 821. According to an embodiment, the fourth adhesive film 87 may have a specified thickness to ensure the performance of the biometric sensor module 840. The foreign object may be blocked to be entered into a space between the optical filter layer 845 and the panel layer 821 by directly attaching the optical filter layer 845 to the panel layer 821 using the fourth adhesive film 87, thereby ensuring the performance of the biometric sensor.

Figure 9:
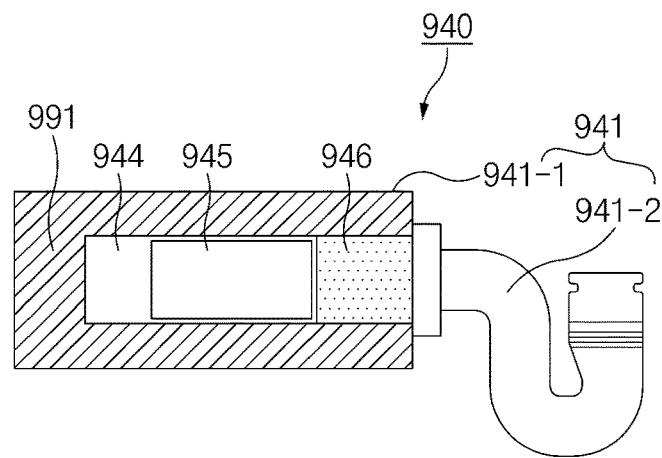
FIG. 9 illustrates a package structure of a biometric sensor module, according to an embodiment.
Figure 9:
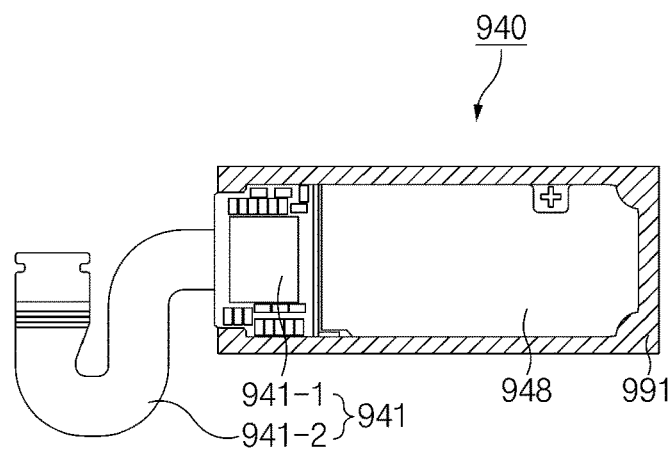
Figure 9:
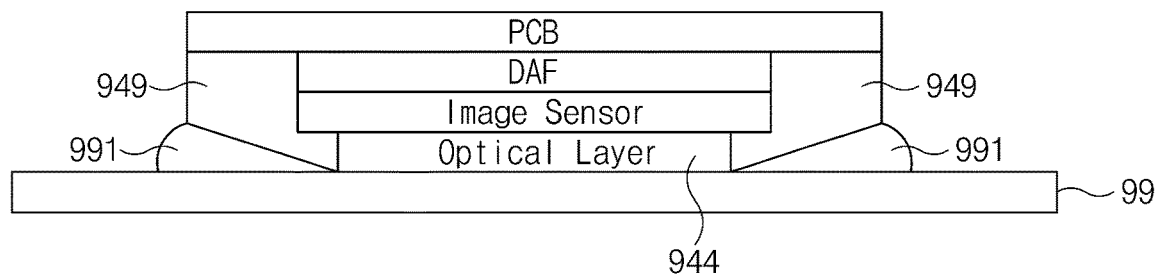

FIG. 9 illustrates a package structure of a biometric sensor module, according to an embodiment.

<91> image of FIG. 9 illustrates an example of the front view of a biometric sensor module 940; <92> image illustrates an example of the rear view of the biometric sensor module 940; <93> image illustrates an example of the sectional view of the biometric sensor module 940.

Referring to FIG. 9, the biometric sensor module 940 (e.g., the biometric sensor module 701) may include a circuit board 941 (e.g., a circuit board 741), an optical layer 944 (e.g., the optical layer 744), an optical filter layer 945 (e.g., the optical filter layer 745), a magnetic screen layer 948 (e.g., a magnetic metal powder sheet) (e.g., the magnetic screen layer 748), and a protection member 949 (e.g., the protection member 749). According to various embodiments, the biometric sensor module 940 may be implemented without some of the elements illustrated in FIG. 9 or may be implemented to further include one or more elements not illustrated in FIG. 9.

According to an embodiment, a first adhesive member 991 may be disposed in the biometric sensor module 940. According to an embodiment, the first adhesive member 991 may be disposed adjacent to the protection member 949. The protection member 949 may have a structure tilted such that the height of the protection member 649 decreases as it goes towards the periphery of the biometric sensor module 940. It may be difficult to attach the protection member 949 to a display (e.g., the display 320 of FIG. 3) due to the structural feature of the protection member 949. As such, the first adhesive member 991 may be disposed in the biometric sensor module 940 to compensate for the tilted structure of the protection member 949. According to an embodiment, the first adhesive member 991 may be disposed at least one edge of the protection member 949. For example, referring to <91> image and <92> image of FIG. 9, the first adhesive member 991 may be disposed at the remaining edges other than the edge in the direction in which a FPCB 941-2 is located.

Referring to <93> image of FIG. 9, for the purpose of preventing the first adhesive member 991 from entering the optical layer 944 and to evenly form the first adhesive member 991, the first adhesive member 991 may be formed between the protection member 949 and a release film 99 after the release film 99 is attached to the optical layer 944 in the process of forming the first adhesive member 991. The release film 99 may be removed after the first adhesive member 991 is formed between the protection member 949 and the release film 99. According to an embodiment, the first adhesive member 991 may include ultraviolet rays (UV) glue capable of being cured by UV light, such as UV ink or UV curable resin. For example, after the first adhesive member 991 is applied between the protection member 949 and the release film 99, the polymerization may be initiated by UV light to fix the first adhesive member 991.

Referring to <91> image of FIG. 9, a screen member 946 may be disposed at the biometric sensor module 940. For example, the screen member 946 may be disposed at the edge where the FPCB 941-2 is located, so as to be adjacent to the protection member 949 and the first adhesive member 991. Because the first adhesive member 991 is not easily formed at the edge where the FPCB 941-2 is located, the screen member 946 may be disposed instead of the first adhesive member 991. For example, the screen member 946 may include polyurethane (e.g., poron) and/or rubber. For example, the screen member 946 may be attached on the protection member 949 by an adhesive film (e.g., DAF).

Figure 10:
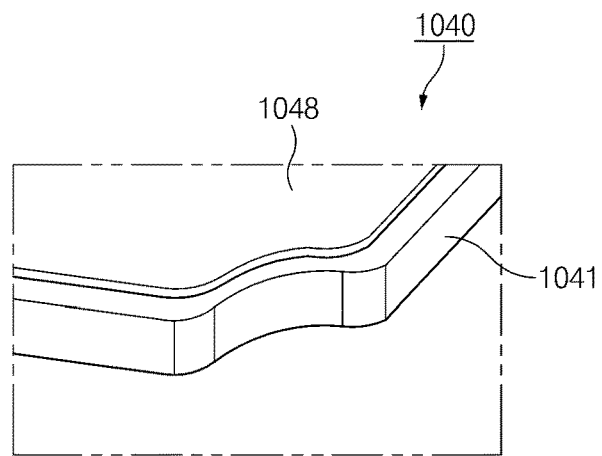
FIG. 10 illustrates a part of a package structure of a biometric sensor module, according to an embodiment.
Figure 10:
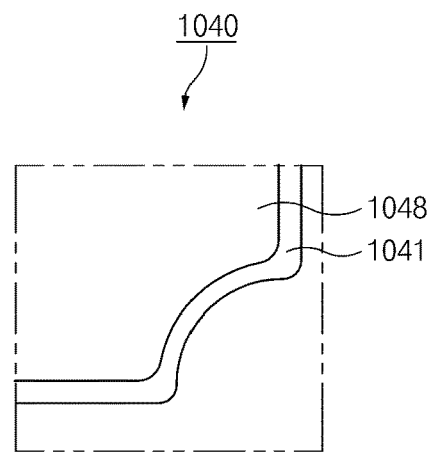
Figure 10:
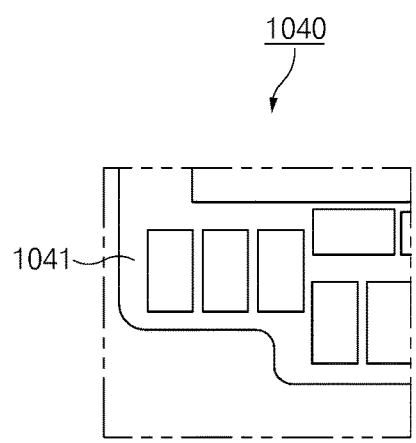

FIG. 10 illustrates a part of a package structure of a biometric sensor module, according to an embodiment.

<1001> image of FIG. 10 illustrates a perspective view of the first side corner portion when the rear surface of a biometric sensor module (e.g., a biometric sensor) 1040 (e.g., the biometric sensor module 940) is viewed; <1002> image illustrates a rear view of the first side corner portion of the biometric sensor module 1040; <1003> image illustrates a rear view of the second side corner portion of the biometric sensor module 1040.

Referring to FIG. 10, the biometric sensor module 1040 may include a circuit board 1041 (e.g., the circuit board 641) and a magnetic screen layer 1048 (e.g., the magnetic screen layer 648). According to an embodiment, the corners of the circuit board 1041 may have an inwardly concave shape. As the corners of the circuit board 1041 have an inwardly concave shape, when a second adhesive member (e.g., a second adhesive member 1193 or 1293 of FIG. 11 or 12) is applied, the second adhesive member may be effectively applied on a first adhesive member (e.g., a first adhesive member 1191 or 1291 of FIG. 11 or 12).

Figure 11:
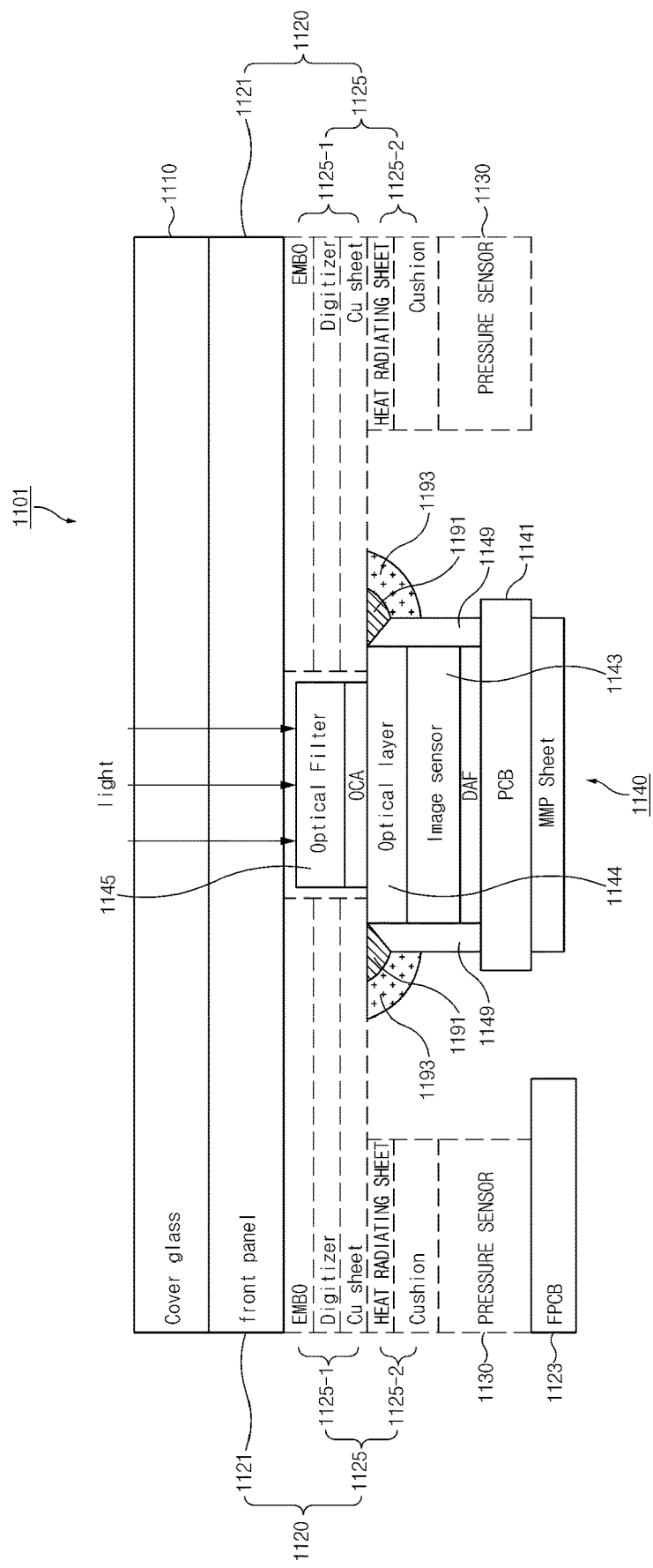
FIG. 11 is a sectional view of an electronic device, according to an embodiment.

FIG. 11 is a sectional view of an electronic device, according to an embodiment.

The sectional view illustrated in FIG. 11 corresponds to a sectional view in a state where a biometric sensor module 1140 is attached to a display 1120. Referring to FIG. 11, an electronic device 1101 (e.g., the electronic device 301 of FIG. 3) may include a cover glass 1110 (e.g., the cover glass 310 of FIG. 3), a display (or a display panel) 1120 (e.g., the display 320 of FIG. 3), a pressure sensor 1130 (e.g., the pressure sensor 330 of FIG. 3), and the biometric sensor module 1140 (e.g., the biometric sensor module 340 of FIG. 3).

According to an embodiment, the biometric sensor module 1140 may pass through the sensor-positioned area (e.g., the sensor-positioned area 427 of FIG. 4A) formed on the display 1120 and the sensor-positioned area (e.g., the sensor-positioned area 431 of FIG. 4A) formed on the pressure sensor 1130 to be attached to the rear surface of the display 1120. For example, the first adhesive member 1191 formed on a protection member 1149 of the biometric sensor module 1140 and the partial area (e.g., an edge area) of an optical layer 1144 may be attached to the rear surface of a first layer 1125-1 of a layer 1125.

In a state where the first adhesive member 1191 and the partial area of the optical layer 1144 are attached to the rear surface of the first layer 1125-1, the biometric sensor module 1140 may be fixed to the display 1120 by the second adhesive member 1193. For example, the second adhesive member 1193 may be applied to the first adhesive member 1191 so as to be adjacent to the protection member 1149 and the rear surface of the first layer 1125-1. According to an embodiment, the second adhesive member 1193 may be applied to at least part of edges of the biometric sensor 1140. For example, the second adhesive member 1193 may be applied through at least part of the corner areas of the circuit board 1141. For another example, the second adhesive member 1193 may be applied to all areas of the first adhesive member 1191.

According to an embodiment, in a state where the biometric sensor module 1140 is attached to the display 1120, the biometric sensor module 1140 (e.g., an image sensor 1143, the optical layer 1144, and an optical filter layer 1145) may face a panel layer 1121. According to an embodiment, the optical filter layer 1145 may be positioned spaced by a specified distance from the panel layer 1121 to ensure the performance of the biometric sensor module 1140. The space between the optical filter layer 1145 and the panel layer 1121 may be blocked from the outside by the first adhesive member 1191 and the second adhesive member 1193 (additionally, a screen member (e.g., the screen member 946 of FIG. 9)) to prevent a foreign object from entering and to ensure the performance of the biometric sensor.

Figure 12:
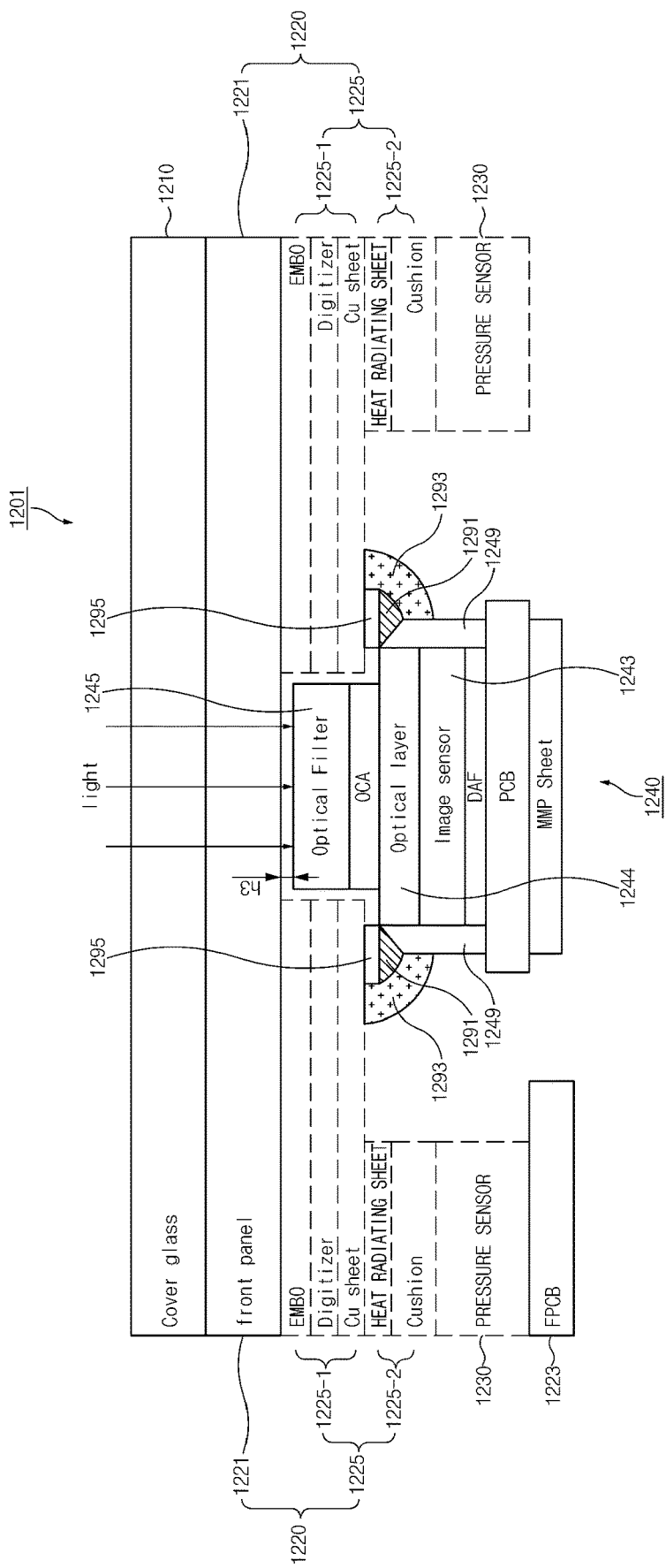
FIG. 12 illustrates a sectional view of the electronic device according to an embodiment.

FIG. 12 illustrates a sectional view of the electronic device according to an embodiment.

The sectional view illustrated in FIG. 12 corresponds to a sectional view in a state where a biometric sensor module 1240 is attached to a display 1220. Referring to FIG. 12, an electronic device 1201 (e.g., the electronic device 301 of FIG. 3) may include a cover glass 1210 (e.g., the cover glass 310 of FIG. 3), the display (or a display panel) 1220 (e.g., the display 320 of FIG. 3), a pressure sensor 1230 (e.g., the pressure sensor 330 of FIG. 3), and the biometric sensor module 1240 (e.g., the biometric sensor module 340 of FIG. 3).

According to an embodiment, the biometric sensor module 1240 may pass through the sensor-positioned area (e.g., the sensor-positioned area 427 of FIG. 4A) formed on the display 1220 and the sensor-positioned area (e.g., the sensor-positioned area 431 of FIG. 4A) formed on the pressure sensor 1230 to be attached to the rear surface of the display 1220. For example, a first adhesive member 1291 (e.g., the first adhesive member 1191) formed on a protection member 1249 of the biometric sensor module 1240 may be attached to the rear surface of a first layer 1225-1 of a layer 1225. For example, the first adhesive member 1291 may be attached to the rear surface of the first layer 1225-1 by a fifth adhesive film 1295 interposed between the first adhesive member 1291 and the first layer 1225-1. For example, the fifth adhesive film 1295 may be attached to the partial area of an optical layer 1244 as well as the first adhesive member 1291.

After the first adhesive member 1291 is attached to the rear surface of the first layer 1225-1 by the fifth adhesive film 1295, the biometric sensor module 1240 may be fixed to the display 1220 by a second adhesive member 1293. For example, the second adhesive member 1293 (e.g., the second adhesive member 1193) may be applied to the first adhesive member 1291 so as to be adjacent to the protection member 1249 and the rear surface of the first layer 1225-1. According to an embodiment, the second adhesive member 1293 may be applied to at least part of edges of the biometric sensor 1240. Because the biometric sensor module 1240 is doubly attached to the display 1220 by the fifth adhesive film 1295 and the second adhesive member 1193, the adhesion of the biometric sensor module 1240 may be improved.

According to an embodiment, in a state where the biometric sensor module 1240 is attached to the display 1220, the biometric sensor module 1240 (e.g., an image sensor 1243, the optical layer 1244, and an optical filter layer 1245) may face a panel layer 1221. According to an embodiment, the optical filter layer 1245 may be positioned spaced by a specified distance from the panel layer 1221 to ensure the performance of the biometric sensor module 1240. The space between the optical filter layer 1245 and the panel layer 1221 may be blocked from the outside by the first adhesive member 1191, the second adhesive member 1193, and the fifth adhesive film 1295 (additionally, a screen member (e.g., the screen member 946 of FIG. 9)) to prevent a foreign object from entering and to ensure the performance of the biometric sensor.

The electronic device according to various embodiments disclosed in the disclosure may be various types of devices. For example, the electronic device may include at least one of a portable communication device (e.g., a smartphone), a computer device (e.g., a personal digital assistant (PDA), a tablet personal computers (PC), a laptop PC, a desktop PC, a workstation, or a server), a portable multimedia device (e.g., an e-book reader or an MP3 player), a portable medical device (e.g., a heart rate, blood glucose, blood pressure, or a thermometer), a camera, or a wearable device. The wearable device may include at least one of an accessory-type device (e.g., a timepiece, a ring, a bracelet, an anklet, a necklace, glasses, a contact lens, or a head-mounted device (HMD)), one-piece fabric or clothes type device (e.g., electronic clothes), a body-attached type device (e.g., a skin pad or a tattoo), or a bio-implantable type device (e.g., implantable circuit). According to an embodiment, the electronic device may include at least one of, for example, a televisions, a digital video disc (DVD) player, an audio device, an audio accessory device (e.g., a speaker, a head phone, or a headset), a refrigerator, an air conditioner, a cleaner, an oven, a microwave oven, a washing machine, an air cleaner, a set-top box, a home automation control panel, a security control panel, a game console, an electronic dictionary, an electronic key, a camcorder, or an electronic picture frame.

According to another embodiment, the electronic device may include at least one of a navigation device, a global navigation satellite system (GNSS), an event data recorder (EDR) (e.g., a black box for a car, a ship, or a plane), a vehicle infotainment device (e.g., a head-up display for vehicle), an industrial or home robot, a drone, an automatic teller's machine (ATM), a points of sales (POS) device, a measuring instrument (e.g., a water, electricity, or gas measuring instrument), or an Internet of things device (e.g., a light bulb, a sprinkler device, a fire alarm, a thermostat, or a street lamp). According to an embodiment of the disclosure, the electronic device may not be limited to the above-described electronic devices. In addition, for example, as in the case of a smartphone equipped with a measurement function of personal biometric information (e.g., heartbeat or blood sugar), the electronic device may complexly provide the functions of a plurality of devices. The term "user" used herein may refer to a person who uses an electronic device or may refer to a device (e.g., an artificial intelligence electronic device) that uses an electronic device.

Various embodiments of the disclosure and terms used herein are not intended to limit the technologies described in the disclosure to specific embodiments, and it should be understood that the embodiments and the terms include modification, equivalent, and/or alternative on the corresponding embodiments described herein. With regard to description of drawings, similar components may be marked by similar reference numerals. The terms of a singular form may include plural forms unless otherwise specified. In the disclosure disclosed herein, the expressions "A or B", "at least one of A and/or B", "A, B, or C", or "at least one of A, B, and/or C", and the like used herein may include any and all combinations of one or more of the associated listed items. Expressions such as "first," or "second," and the like, may express their components regardless of their priority or importance and may be used to distinguish one component from another component but is not limited to these components. When a (e.g., first) component is referred to as being "(operatively or communicatively) coupled with/to" or "connected to" another (e.g., second) component, it may be directly coupled with/to or connected to the other component or an intervening component (e.g., a third component) may be present.

According to the situation, the expression "adapted to or configured to" used herein may be interchangeably used as, for example, the expression "suitable for", "having the capacity to", "changed to", "made to", "capable of" or "designed to". The expression "a device configured to" may mean that the device is "capable of" operating together with another device or other parts. For example, a "processor configured to (or set to) perform A, B, and C" may mean a dedicated processor (e.g., an embedded processor) for performing corresponding operations or a generic-purpose processor (e.g., a central processing unit (CPU) or an application processor) which performs corresponding operations by executing one or more software programs which are stored in a memory device (e.g., the memory 130).

The term "module" used herein may include a unit, which is implemented with hardware, software, or firmware, and may be interchangeably used with the terms "logic", "logical block", "part", "circuit", or the like. The "module" may be a minimum unit of an integrated part or a part thereof or may be a minimum unit for performing one or more functions or a part thereof. For example, the module may be composed of an application-specific integrated circuit (ASIC) or field-programmable gate arrays (FPGAs).

According to various embodiments, at least part of a device or a method may be implemented by instructions stored in a computer-readable storage media (e.g., the internal memory 136 or the external memory 138) in the form of a program. The instructions, when executed by a processor (e.g., the processor 120), may cause the processor to perform a function corresponding to the instructions, directly or by using other components under the control of the processor. The instructions may include the code generated or executed by a compiler or an interpreter.

Each element (e.g., a module or a program) according to various embodiments may be composed of single entity or a plurality of entities, a part of the above-described sub-elements may be omitted or may further include other elements. Alternatively or additionally, some components (e.g., a module or a program) may be combined with each other so as to form one entity, so that the functions of the components may be performed in the same manner as before the combination. According to various embodiments, operations executed by modules, program modules, or other components may be executed by a successive method, a parallel method, a repeated method, or a heuristic method. Alternatively, at least some of the operations may be executed in another order or may be omitted, or any other operation may be added.

The invention claimed is:

1. An electronic device comprising:
   a display panel;
   a biometric sensor module disposed apart from a rear surface of the display panel such that a gap is formed between an optical filter of the biometric sensor and the rear surface of the display panel;
   a processor electrically connected to the display panel and the biometric sensor module and configured to obtain biometric information, using the biometric sensor module;
   a first adhesive member disposed so as to fill at least part of the gap; and
   a second adhesive member applied on the first adhesive member,
   wherein the biometric sensor module is attached to the rear surface of the display panel by the second adhesive member.

2. The electronic device of claim 1, further comprising:
   a third adhesive member interposed between the rear surface of the display panel and the first adhesive member and bonding the biometric sensor module to the rear surface of the display panel.

3. The electronic device of claim 1, wherein the biometric sensor module includes:
   a first circuit board;
   an image sensor disposed on the first circuit board and configured to obtain the biometric information; and
   an optical layer disposed on at least part of an area of the image sensor,
   wherein at least part of the optical layer included in the biometric sensor module is attached to the rear surface of the display panel.

4. The electronic device of claim 3, wherein the biometric sensor module further includes:
   an optical filter layer disposed on at least part of an area of the optical layer,
   wherein the optical filter layer is disposed to face the rear surface of the display panel.

5. The electronic device of claim 4, further comprising:
   a fourth adhesive member visually transparent between the optical filter layer and the rear surface of the display panel,
   wherein the fourth adhesive member is interposed between the optical filter layer and the rear surface of the display panel.

6. The electronic device of claim 5, wherein the biometric sensor module further includes:
   a conductive wire electrically connecting the image sensor to the first circuit board; and a protection member covering the conductive wire in a space formed by the first circuit board and the image sensor.

7. The electronic device of claim 5, wherein the first circuit board includes:
a flexible board formed extending from the first circuit board,
wherein a connecting part for connecting the first circuit board to another circuit board is formed on the flexible board.

8. The electronic device of claim 1, further comprising:
a screen member, which is adjacent to the first adhesive member, which is interposed between the rear surface of the display panel and an upper surface of the biometric sensor module, and which fills the gap.

9. The electronic device of claim 1,
wherein the display panel includes:
a flexible board extending to an outside of the display panel from a board layer formed as at least part of the display panel,
wherein the biometric sensor module is disposed on the flexible board.

10. The electronic device of claim 2, wherein a corner of the first circuit board has an inwardly concave shape, and
wherein the second adhesive member is applied through a portion of the corner of the first circuit board.

11. The electronic device of claim 1, wherein the display panel includes:
a panel layer including at least one pixel; and
a layer disposed under the panel layer,
wherein an opening is formed in an area of the layer that faces the biometric sensor module.

12. The electronic device of claim 11, wherein the layer includes:
a first layer including a first opening; and
a second layer disposed under the first layer and including a second opening,
wherein the biometric sensor module is disposed to face the first opening of the first layer,
wherein the first adhesive member fills the gap formed between the first layer and the biometric sensor module, and
wherein the biometric sensor module is attached to the first layer, using the second adhesive member.

13. The electronic device of claim 11, wherein the second adhesive member is applied between an outer side surface of the biometric sensor module and an inter side surface of the opening of the layer.

14. The electronic device of claim 1, wherein the processor is configured to:
obtain the biometric information about an external object, using reflected light, which is obtained as light from an emitting element included in the display panel is reflected by the external object, and using the biometric sensor module.

15. A display device comprising:
a display panel;
a biometric sensor module disposed apart from a rear surface of the display panel such that a gap is formed between an optical filter of the biometric sensor and the rear surface of the display panel;
a processor electrically connected to the display panel and the biometric sensor module and configured to obtain biometric information, using the biometric sensor module;
a first adhesive member disposed so as to fill at least part of the gap; and
a second adhesive member applied on the first adhesive member,
wherein the biometric sensor module is attached to the rear surface of the display panel by the second adhesive member.

* * * * *